(12) United States Patent
Oberegger et al.

(10) Patent No.: US 7,537,784 B2
(45) Date of Patent: May 26, 2009

(54) MODIFIED RELEASE TABLET OF BUPROPION HYDROCHLORIDE

(75) Inventors: Werner Oberegger, Mississauga (CA); Okponanabofa Eradiri, Ashburn, VA (US); Fang Zhou, Centreville, VA (US); Paul Maes, Toronto (CA)

(73) Assignee: Biovail Laboratories International SRL, St. Michael (BB)

( * ) Notice: Subject to any disclaimer, the term of this patent is extended or adjusted under 35 U.S.C. 154(b) by 302 days.

(21) Appl. No.: 11/451,496

(22) Filed: Jun. 13, 2006

(65) Prior Publication Data

US 2006/0228415 A1 Oct. 12, 2006

Related U.S. Application Data

(63) Continuation of application No. 10/507,525, filed as application No. PCT/US03/24700 on Aug. 8, 2003, now abandoned.

(51) Int. Cl.
*A61K 9/20* (2006.01)
*A61K 9/22* (2006.01)
*A61K 9/24* (2006.01)
*A61K 9/28* (2006.01)
*A61K 9/30* (2006.01)
*A61K 9/36* (2006.01)
*A61K 9/42* (2006.01)

(52) U.S. Cl. .................. 424/468; 424/464; 424/465; 424/472; 424/474; 424/475; 424/476; 424/479; 424/480

(58) Field of Classification Search .............. None
See application file for complete search history.

(56) References Cited

U.S. PATENT DOCUMENTS

| | | | |
|---|---|---|---|
| 3,885,046 A | 5/1975 | Mehta | |
| 4,361,545 A | 11/1982 | Powell et al. | |
| 4,711,782 A | 12/1987 | Okada et al. | |
| 4,713,248 A | 12/1987 | Kojorn et al. | |
| 4,769,027 A | 9/1988 | Baker et al. | |
| 4,792,452 A | 12/1988 | Howard et al. | |
| 4,795,641 A | 1/1989 | Kashdan | |
| 4,795,643 A | 1/1989 | Seth | |
| 4,797,286 A | 1/1989 | Thakkar et al. | |
| 4,806,337 A | 2/1989 | Snipes et al. | |
| 4,834,985 A | 5/1989 | Lelger et al. | |
| 4,837,980 A | 6/1989 | Rogers, Jr. | |
| 4,847,092 A | 7/1989 | Thakkar et al. | |
| 4,851,229 A | 7/1989 | Magruder et al. | |
| 4,860,662 A | 8/1989 | Matsumoto et al. | |
| 4,880,622 A | 11/1989 | Allcuck et al. | |
| 4,882,167 A | 11/1989 | Jang | |
| 5,030,457 A | 7/1991 | Ng et al. | |
| 5,047,248 A | 9/1991 | Calanchi et al. | |
| 5,082,655 A | 1/1992 | Snipes et al. | |
| 5,126,646 A | 6/1992 | Fujita et al. | |
| RE33,994 E | 7/1992 | Baker et al. | |
| 5,169,638 A | 12/1992 | Dennis et al. | |
| 5,187,150 A | 2/1993 | Speiser et al. | |
| 5,200,193 A | 4/1993 | Radebaugh et al. | |
| 5,283,065 A | 2/1994 | Doyon et al. | |
| 5,391,777 A | 2/1995 | Tanabe et al. | |
| 5,427,798 A | 6/1995 | Ludwig et al. | |
| 5,431,922 A | 7/1995 | Nicklasson | |
| 5,462,747 A | 10/1995 | Radebaugh et al. | |
| 5,478,572 A | 12/1995 | David et al. | |
| 5,523,095 A | 6/1996 | Wilson et al. | |
| 5,558,879 A | 9/1996 | Chen et al. | |
| 5,582,837 A | 12/1996 | Shell | |
| 5,603,953 A | 2/1997 | Herbig et al. | |
| 5,614,218 A | 3/1997 | Olsson et al. | |
| 5,648,096 A | 7/1997 | Gander et al. | |
| 5,654,005 A | 8/1997 | Chen et al. | |
| 5,733,577 A | 3/1998 | Myers et al. | |
| 5,762,950 A | 6/1998 | Yli-Urpo et al. | |
| 5,762,961 A | 6/1998 | Roser et al. | |
| 5,763,493 A | 6/1998 | Ruff et al. | |
| 5,840,334 A | 11/1998 | Raiden et al. | |
| 5,876,752 A | 3/1999 | Herbig et al. | |
| 5,888,542 A | 3/1999 | de Barochez et al. | |
| 5,890,334 A | 4/1999 | Hughes et al. | |
| 5,919,484 A | 7/1999 | Shih et al. | |
| 5,952,005 A | 9/1999 | Olsson et al. | |

(Continued)

FOREIGN PATENT DOCUMENTS

CA    1321754    8/1993

(Continued)

OTHER PUBLICATIONS

Hawley's Condensed Chemical Dictionary, 12th Edition, pp. 1088, 1993.

(Continued)

*Primary Examiner*—S. Tran
(74) *Attorney, Agent, or Firm*—Oblon, Spivak, McClelland, Maier & Neustadt, P.C

(57) ABSTRACT

A modified-release tablet of bupropion hydrochloride comprising (i) a core comprising an effective amount of bupropion hydrochloride, a binder, a lubricant; and (ii) a control releasing coat surrounding said core; and (iii) a moisture barrier surrounding said control releasing coat, wherein the modified-release tablet is bioequivalent to Wellbutrin® or Zyban®/Wellbutrin®SR tablets.

16 Claims, 14 Drawing Sheets

U.S. PATENT DOCUMENTS

| | | | |
|---|---|---|---|
| 5,958,458 | A | 9/1999 | Norling et al. |
| 6,004,582 | A | 12/1999 | Faour et al. |
| 6,020,002 | A | 2/2000 | Myers |
| 6,022,562 | A | 2/2000 | Autant et al. |
| 6,033,685 | A | 3/2000 | Qiu et al. |
| 6,033,686 | A | 3/2000 | Seth |
| 6,036,976 | A | 3/2000 | Takechi et al. |
| 6,096,339 | A | 8/2000 | Ayer et al. |
| 6,096,341 | A | 8/2000 | Seth |
| 6,113,943 | A | 9/2000 | Okada et al. |
| 6,117,452 | A | 9/2000 | Ahlgren et al. |
| 6,120,803 | A | 9/2000 | Wong et al. |
| 6,129,931 | A | 10/2000 | Nerella et al. |
| 6,143,325 | A | 11/2000 | Dennis et al. |
| 6,143,327 | A | 11/2000 | Seth |
| 6,153,223 | A | 11/2000 | Apelian et al. |
| 6,159,501 | A | 12/2000 | Skinhoj |
| 6,183,780 | B1 | 2/2001 | Van Balken et al. |
| 6,197,827 | B1 | 3/2001 | Cary |
| 6,210,716 | B1 | 4/2001 | Chen et al. |
| 6,221,917 | B1 | 4/2001 | Maitra et al. |
| 6,238,697 | B1 | 5/2001 | Kumar et al. |
| 6,270,805 | B1 | 8/2001 | Chen et al. |
| 6,274,171 | B1 | 8/2001 | Sherman et al. |
| 6,287,587 | B2 | 9/2001 | Shigeyuki et al. |
| 6,306,436 | B1 | 10/2001 | Chungi et al. |
| 6,319,520 | B1 | 11/2001 | Wuthrich et al. |
| 6,340,475 | B2 | 1/2002 | Shell et al. |
| 6,340,476 | B1 | 1/2002 | Midha et al. |
| 6,342,249 | B1 | 1/2002 | Wong et al. |
| 6,342,250 | B1 | 1/2002 | Masters |
| 6,352,721 | B1 | 3/2002 | Faour |
| 6,355,272 | B1 | 3/2002 | Caramella et al. |
| 6,363,626 | B1 | 4/2002 | Bhatt et al. |
| 6,387,403 | B1 | 5/2002 | Seroff et al. |
| 6,391,336 | B1 | 5/2002 | Royer |
| 6,395,300 | B1 | 5/2002 | Straub et al. |
| 6,419,952 | B2 | 7/2002 | Wong et al. |
| 6,440,457 | B1 | 8/2002 | Edgren et al. |
| 6,441,046 | B1 | 8/2002 | Mendel et al. |
| 6,475,321 | B1 | 11/2002 | Ikeda et al. |
| 6,475,521 | B1 | 11/2002 | Timmins et al. |
| 6,482,987 | B2 | 11/2002 | Kulkarni et al. |
| 6,488,962 | B1 | 12/2002 | Berner et al. |
| 6,491,947 | B2 | 12/2002 | Moore et al. |
| 6,495,605 | B2 | 12/2002 | McCullough et al. |
| 6,500,459 | B1 | 12/2002 | Chhabra et al. |
| 6,517,866 | B1 | 2/2003 | Ende et al. |
| 6,534,089 | B1 | 3/2003 | Ayer et al. |
| 6,541,532 | B1 | 4/2003 | Ragsdale et al. |
| 6,548,084 | B2 | 4/2003 | Leonard et al. |
| 6,555,136 | B2 | 4/2003 | Midha |
| 6,558,708 | B1 | 5/2003 | Lin |
| 6,565,883 | B2 | 5/2003 | Ogorka et al. |
| 6,569,463 | B2 | 5/2003 | Patel et al. |
| 6,589,553 | B2 | 7/2003 | Li et al. |
| 6,599,529 | B1 | 7/2003 | Skinhøj |
| 6,635,281 | B2 | 10/2003 | Wong |
| 6,641,614 | B1 | 11/2003 | Wagner et al. |
| 6,682,759 | B2 | 1/2004 | Lim et al. |
| 6,723,340 | B2 | 4/2004 | Gusler et al. |
| 6,730,321 | B2 | 5/2004 | Ting et al. |
| 6,797,283 | B1 | 9/2004 | Edgren et al. |
| 6,905,708 | B2 | 6/2005 | Li et al. |
| 2001/0018070 | A1 | 8/2001 | Shell et al. |
| 2002/0044960 | A1 | 4/2002 | Cherukuri |
| 2002/0047058 | A1 | 4/2002 | Verhoff et al. |
| 2002/0197311 | A1 | 12/2002 | Hasenzahl et al. |
| 2003/0003151 | A1 | 1/2003 | Chopra |
| 2003/0044462 | A1 | 3/2003 | Subramanian et al. |
| 2003/0059471 | A1 | 3/2003 | Compton et al. |
| 2003/0064097 | A1 | 4/2003 | Patel et al. |
| 2003/0064104 | A1 | 4/2003 | Stillman |
| 2003/0072802 | A1 | 4/2003 | Cutler |
| 2003/0091630 | A1 | 5/2003 | Louie-Helm |
| 2003/0104048 | A1 | 6/2003 | Patel et al. |
| 2003/0104052 | A1 | 6/2003 | Berner et al. |
| 2003/0133982 | A1 | 7/2003 | Heimlich et al. |
| 2003/0134906 | A1 | 7/2003 | Valducci et al. |
| 2003/0147952 | A1 | 8/2003 | Lim et al. |
| 2003/0152662 | A1 | 8/2003 | Louie-Helm et al. |
| 2003/0161874 | A1* | 8/2003 | Li et al. ............... 424/465 |
| 2003/0198683 | A1 | 10/2003 | Li et al. |
| 2003/0232080 | A1 | 12/2003 | Pather et al. |
| 2004/0022844 | A1 | 2/2004 | Hasenzahl et al. |
| 2004/0022852 | A1 | 2/2004 | Chopra |
| 2004/0037879 | A1 | 2/2004 | Adusumilli |
| 2004/0037883 | A1 | 2/2004 | Zhou et al. |
| 2004/0059002 | A1 | 3/2004 | Couch et al. |
| 2004/0115263 | A1 | 6/2004 | Robertson et al. |
| 2004/0121010 | A1 | 6/2004 | Hirsh et al. |
| 2004/0132826 | A1 | 7/2004 | Hirsh et al. |
| 2004/0141925 | A1 | 7/2004 | Bosch et al. |
| 2004/0156872 | A1 | 8/2004 | Bosch et al. |
| 2004/0156899 | A1 | 8/2004 | Louie-Helm |
| 2004/0185097 | A1 | 9/2004 | Kannan et al. |
| 2004/0220274 | A1 | 11/2004 | Sobolov-Jaynes |
| 2004/0225020 | A1 | 11/2004 | McCullough et al. |
| 2004/0228915 | A1 | 11/2004 | Noack et al. |
| 2004/0229942 | A1 | 11/2004 | Hassman et al. |

FOREIGN PATENT DOCUMENTS

| | | |
|---|---|---|
| CA | 2286684 | 10/1998 |
| CA | 2318960 | 8/1999 |
| CA | 2259730 | 7/2000 |
| CA | 2433915 | 8/2002 |
| WO | WO 99/33456 | 7/1999 |
| WO | WO 99/38499 | 8/1999 |
| WO | WO 00/64773 | 9/2000 |
| WO | WO 02/094323 | 11/2002 |
| WO | WO 03/015795 | 2/2003 |
| WO | WO 03/086362 | 10/2003 |

OTHER PUBLICATIONS

Handbook of Pharmaceutical Excipients 2$^{nd}$ Edition, pp. 211-212 and 355-357, 1994.

Hui, et al., "Design and Fabrication of Oral Controlled Release Drug Delivery Systems", Controlled Drug Delivery: Fundamentals and Applications, edited by J. R. Robinson & Vincent H. L. Lee, 2$^{nd}$ Edition, Chapter 9, pp. 373-432, 1987.

Porter, Controlled-Release Film Coatings Based on Ethylcellulose, Drug Development and Industrial Pharmacy, vol. 15, No. 10, pp. 1495-1521, 1989.

Volker Bühler, Generic Drug Formulations, 2$^{nd}$ Edition, No. 3.5, 1998.

Remington: the Science and Practice of Pharmacy, 19$^{th}$ Edition, Mack Publishing Company, vol. II, Chapter 93 and Chapter 94, pp. 1650-1675, 1995.

The DOW Chemical Company, ETHOCEL Premium Polymers for Phamaceutical Applications, Oct. 1998.

* cited by examiner

MODIFIED RELEASE TABLET OF BUPROPION HYDROCHLORIDE

FIELD OF THE INVENTION

The present invention relates to a modified-release tablet of pharmaceutically acceptable salts of bupropion, preferably bupropion hydrochloride.

BACKGROUND

Bupropion is an antidepressant chemically unrelated to tricyclics, tetracyclics, selective serotonin re-uptake inhibitors (SSRIs), or other known antidepressant agents. The drug resembles a psycho stimulant in terms of its neurochemical and behavioral profiles in vivo, but it does not reliably produce stimulant-like effects in humans at clinically prescribed doses. Its structure closely resembles that of diethylpropion and it is related to phenylethylamines. It is designated as (±)-1-(3-chlorophenyl)-2-[(1,1-dimethylethyl)amino]-1-propanone hydrochloride and by its generic name amfebutamone hydrochloride. Bupropion hydrochloride is commercially available as an immediate release form (Wellbutrin®) and a sustained release form (Wellbutrin® SR and Zyban®). Both Wellbutrin® SR and Zyban® are chemically and pharmaceutically identical.

The neurochemical mechanism of the antidepressant effect of bupropion is not well known. Bupropion does not inhibit monoamine oxidase. Bupropion affects chemicals within the brain that nerves use to send messages to each other. These chemical messengers are called neurotransmitters. The neurotransmitters that are released by nerves are taken up again by the nerves that release them for reuse (This is referred to as reuptake). Many experts believe that depression is caused by an imbalance among the amounts of neurotransmitters that are released. It is believed that bupropion works by inhibiting the reuptake of the neurotransmitters dopamine, serotonin, and norepinephrine, an action which results in more dopamine, serotonin, and norepinephrine made available to transmit messages to other nerves. Accordingly, bupropion is unique in that its major effect is on dopamine, an effect, which is not shared by the SSRIs (e.g. paroxetine (Paxil®), fluoxetine (Prozac®), sertraline (Zoloft®)) or the tricyclic antidepressants or TCAs (e.g. amitriptyline (Elavil®), imipramine (Tofranil®), desipramine (Norpramin®)).

Wellbutrin® and Wellbutrin® SR are used for the management of depression. Zyban® has been approved as an aid to patients wanting to quit smoking. Wellbutrin®, the immediate release formulation of bupropion, is dosed three times a day, preferably with 6 or more hours in between doses. For patients requiring more that 300 mg bupropion a day, each dose should not exceed 150 mg. This requires administration of the tablets at least 4 times a day with at least 4 hours in between doses. The immediate release formulation results in more than a 75% release of the bupropion into the dissolution media in about 45 minutes, and one of the major side effects of bupropion has been the incidence of seizures, which in part appears to be strongly associated with the immediate release of the bupropion into the system. Accordingly, sustained release products were developed to avoid the incidence of seizures. The sustained release products are dosed twice daily.

In general, patient compliance is a problem with medications that require a multiple dosing regimen and is especially problematic with depressed individuals. While sustained release formulations have simplified the dosing regimen and increased patient compliance, there is still room for further simplifying the dosing regimen and further improving patient adherence to the dosing regimen. The development of an approved stable once daily modified-release bupropion formulation would be an advance in the art.

Sustained release tablet forms of bupropion have been described in the prior art. U.S. Pat. No. 4,687,660 discloses a tablet formed of a core and a coating, where the core comprises bupropion hydrochloride together with excipient(s) and optionally an osmotic enhancing agent and where the coating comprises a water-insoluble, water-permeable film-forming polymer (such as cellulose acetate), a pore-forming agent (such as impalpable lactose and sodium carbonate), and optionally a so-called water-permeability enhancing agent (such as polyethylene glycol) and again optionally a plasticizer.

U.S. Pat. Nos. 5,358,970 and 5,427,798 describe a sustained release formulation of bupropion hydrochloride based on matrix technology. The term matrix refers to a tablet where the drug is embedded in an excipient that makes a non-disintegrating core called a matrix. Drug diffusion occurs through this core. As bupropion hydrochloride is unstable, the product described in the above two patents requires a stabilizer to achieve sufficient stability. This stabilizer is an acidic compound, preferably cysteine hydrochloride. The major disadvantage of matrix systems is that they generally display a first order release profile. That is, initially drug particles located at the surface of the tablet will be dissolved and drug released rapidly. Thereafter, drug particles at successively increasing distances from the surface of the tablet will be dissolved and released by diffusion in the pores to the exterior of the tablet. Thus, the diffusion distance of the drug will increase as the release process proceeds. It is normally preferred that a zero order or near zero order release profile is obtained rather than a first order release profile. Zero order release system provides a constant rate of drug release over a defined period of time. It is used primarily for drugs with short half-lives so that constant blood levels of the active drug compounds can be maintained with fewer doses.

U.S. Pat. No. 6,589,553 and International Publication No. WO 02/062299 purportedly describes a once daily capsule formulation with two populations of coated pellets, each of which release bupropion hydrochloride at a different pH. One population of pellets is coated to release the drug at a pH corresponding to about 4.8 and lower. The release of the drug from this population of pellets is expected to occur in the upper GI tract. The other population of pellets is coated to release the drug at a pH of 7 and above. The release of bupropion from this population is expected to occur in the lower GI tract. In one example shown, the relative bioavailability of bupropion to Zyban® was only 40% in terms of $C_{max}$ ratio and only 80% in terms of $AUC_{0-inf}$ ratio. In another example shown, the relative bioavailability of bupropion to Zyban® was only 48% and 59% in terms of $C_{max}$ and $AUC_{0-inf}$. The references further describe the introduction of a third population of uncoated active pellets, which purportedly result in a further modification and improvement of the bupropion release. Based on the mean plasma concentration-time profile shown in FIGS. 3 and 4 of these references it is not readily apparent that the introduction of the uncoated active pellets would result in a once daily bioequivalent formulation (reference product is Zyban®). Also, neither one of the two references present any drug stability data.

U.S. Pat. No. 6,033,686 describes a controlled release tablet, free of stabilizer and free of pore forming agent comprising a core consisting essentially of bupropion hydrochloride, a binder and a lubricant; and a coating comprising a water-insoluble, water-permeable film forming polymer, a plasticizer and a water-soluble polymer. The product resulting from the '686 patent is a twice daily product.

U.S. Pat. Nos. 6,096,341 and 6,143,327 both relate to a delayed release formulation of bupropion hydrochloride. The '341 patent provides for a controlled release tablet, free of stabilizer and free of pore forming agent comprising a core consisting essentially of bupropion hydrochloride, a binder and a lubricant; and a coating consisting essentially of a water-insoluble, water-permeable film forming polymer, a plasticizer and a water-soluble polymer. The '327 patent provides for a controlled release tablet, free of stabilizer and free of pore forming agent comprising a core consisting essentially of bupropion hydrochloride, a binder and a lubricant; and a control-releasing coat consisting essentially of a water-insoluble, water-permeable film forming polymer, a plasticizer and a water-soluble polymer and a second coat consisting essentially of a methacrylic polymer and a plasticizer. The formulation as described in the '327 patent does not however, conform to the FDA's guidelines for bioequivalency (see Example 8 herein).

There is currently no approved commercially available stable once daily bupropion dosage form. Accordingly, there is a need for a stable once daily bioequivalent formulation of bupropion or a pharmaceutically acceptable salt thereof.

DEFINITIONS

"Modified release dosage forms" are defined by the USP as those whose drug release characteristics of time course and/or location are chosen to accomplish therapeutic or convenience objectives not offered by conventional forms. An extended-release dosage form allows a twofold reduction in dosing frequency or increase in patient compliance or therapeutic performance. The USP considers that the terms controlled release, prolonged release and sustained release are interchangeable with extended release. Accordingly, the terms "modified-release", controlled-release", "prolonged-release", "extended-release", and "sustained-release" are used interchangeably herein.

The term "pharmaceutically acceptable salt of bupropion" includes salts that are physiologically tolerated by a patient. Such salts are typically prepared from inorganic acids or bases and/or organic acids or bases. Examples of such acids and bases are well known to those of ordinary skill in the art. The invention in particular contemplates the use of bupropion hydrochloride, although the use of other pharmaceutically acceptable salts is within the scope of the invention. The term "effective amount" as used herein means a "pharmaceutically effective amount". A "pharmaceutically effective amount" is the amount or quantity of the pharmaceutically acceptable salt of bupropion, which is sufficient to elicit an appreciable biological response when administered to a patient. It will be appreciated that the precise therapeutic dose will depend on the age and condition of the patient and the nature of the condition to be treated and will be at the ultimate discretion of the attendant physician.

The term "moisture barrier" as used herein is one, which impedes or retards the absorption of moisture. It is known that bupropion hydrochloride is highly hygroscopic and, as such, is relatively unstable and susceptible to decomposition over time especially under high humidity conditions. The proportion of the components of the moisture barrier and the amount of the moisture barrier applied onto the control-releasing coat is such that the moisture barrier does not fall within the USP definition and requirement for and enteric coat. Preferably, the moisture barrier is comprised of an enteric and/or acrylic polymer, preferably an acrylic polymer, optionally a plasticizer, and a permeation enhancer. The permeation enhancer is a hydrophilic substance, which allows water to enter without physical disruption of the coating. The moisture barrier may additionally contain other conventional inert excipients, which may improve processing of the modified-release formulation described herein.

As used herein "total impurities" mean all degradation products resulting from the degradation of bupropion hydrochloride. The "degradation products" include those listed on page 281 of the $26^{th}$ edition of the USP and any other degradation products that may appear as peaks on a chromatogram during the assay.

The modified-release tablets of the invention comprising are bioequivalent to Wellbutrin® or Zyban®/Wellbutrin®SR tablets. The term "bioequivalent" means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug.

SUMMARY OF THE INVENTION

The present invention relates to a modified-release tablet of a pharmaceutically acceptable salt of bupropion, preferably bupropion hydrochloride. The advantage of the modified-release tablets of the invention not afforded by the prior art commercially available Wellbutrin® or Zyban®/Wellbutrin® SR tablets is that the modified-release tablets allow for a once daily administration regimen, is bioequivalent to the commercially available prior art tablets and do not exhibit a food effect.

In accordance with one aspect of the present invention, there is provided a modified-release tablet, comprising (i) a core comprising an effective amount of a pharmaceutically acceptable salt of bupropion, a binder, a lubricant; and (ii) a control-releasing coat surrounding said core; and (iii) a moisture barrier surrounding said control-releasing coat; and; wherein the modified-release tablet is bioequivalent and exhibits a dissolution profile such that after about 2 hours, no more than about 20%, preferably about 2% to about 18%, more preferably about 4% to about 8%, and most preferably about 5% of the bupropion hydrochloride content is released, after about 4 hours, about 15% to about 45%, preferably about 21% to about 37%, more preferably about 28% to about 34%, and most preferably about 32% of the bupropion hydrochloride content is released, after about 8 hours, about 40% to about 90%, preferably about 60% to about 85%, more preferably about 68% to about 74%, and most preferably about 74% of the bupropion hydrochloride content is released and after about 16 hours no less than about 80%, preferably no less than about 93%, more preferably no less than about 96%, and most preferably no less than about 99% of the bupropion hydrochloride content is released.

In one embodiment the moisture barrier does not function as an enteric coat as defined by a USP test, which requires for an enteric layer coated tablet, when placed in 0.1N HCl for one hour, that the total amount of drug released does not exceed 10% and not less than 75% of the drug is released at 45 minutes in pH 6.8 buffer.

In one embodiment of the present invention, the pharmaceutically acceptable salt of bupropion is present at least at about 94% by weight of the dry core weight. Preferably, the modified-release tablet of the present invention contains from about 50 mg to about 450 mg of bupropion hydrochloride. Most preferably, the tablets of the invention contain about 150 mg or 300 mg bupropion hydrochloride.

In another embodiment of the present invention, the amount of binder is present preferably from about 1% to about 6% and more preferably at about 3% by weight of the dry core weight. The binder is preferably polyvinyl alcohol.

In another embodiment of the present invention, the lubricant is present preferably from about 1% to about 6% and more preferably at about 3% by weight of the dry core weight. The lubricants useful for the tablets of the present invention may be selected from the group consisting of glyceryl behenate, stearic acid, hydrogenated vegetable oils and any combination thereof. The preferred lubricant is glyceryl behenate.

In another embodiment of the present invention, the control-releasing coat consists essentially of a water-insoluble water-permeable film-forming polymer and the amount present may vary from about 35% to about 60% by weight of the control-releasing coat dry weight. Preferably, the amount of water-insoluble water-permeable film-forming polymer is present at about 50% by weight of the control-releasing coat dry weight for the 150 mg dose and at about 45% by weight of the control-releasing coat dry weight for the 300 mg dose. The water-insoluble water-permeable film forming polymers may be selected from the group consisting of cellulose ethers, cellulose esters, polyvinyl alcohol and any combination thereof. The preferred water-insoluble water-permeable film forming polymers are the ethyl celluloses and may be selected from the group consisting of ethyl cellulose grade PR 100, ethyl cellulose grade PR 20 and any combination thereof. The preferred water-insoluble water-permeable film-forming polymer is ethyl cellulose grade PR 100.

In another embodiment of the present invention, the amount of plasticizer is present from about 6% to about 30% and more preferably at about 12% by weight of the control-releasing coat dry weight. The plasticizers useful for the tablets of the present invention may be selected from the group consisting of polyols, organic esters, oils/glycerides and any combination thereof. The preferred plasticizer is polyethylene glycol 1450.

In another embodiment of the present invention, the amount of water-soluble polymer present may vary from about 25% to about 50% by weight of the control-releasing coat dry weight. Preferably, the water-soluble polymer is present at about 43% by weight of the control-releasing coat. The water-soluble polymer may be selected from the group consisting of polyvinylpyrrolidone, hydroxypropyl methylcellulose, hydroxypropyl cellulose and any combination thereof. The preferred water-soluble polymer is polyvinylpyrrolidone.

In another embodiment of the present invention, the ratio of the water-insoluble water-permeable film-forming polymer:plasticizer:water-soluble polymer for the 150 mg modified-release bupropion hydrochloride tablet of the invention may vary from about 3:1:4 to about 5:1:3 with the preferred ratio being 4:1:3.

In another embodiment of the present invention, the ratio of the water-insoluble water-permeable film-forming polymer:plasticizer:water-soluble polymer for the 300 mg modified-release bupropion hydrochloride tablet of the invention may vary from about 7:2:6 to about 19:5:18 with the preferred ratio being 13:4:12.

In another embodiment of the present invention, the weight gained after coating the tablet core with the control-releasing coat may vary from 3% to about 30% off the weight of the dry tablet core. For the 150 mg dose of the modified-release tablet of the present invention, the weight gained may vary from about 13% to about 16% of the dry tablet core weight with the preferred weigh gain being about 15% of the weight of the dry tablet core. For the 300 mg dose modified-release tablet of the invention, the weight gained after application of the control-releasing coat may vary from about 8% to about 10% of the dry tablet core weight with a 9% weight gain being preferred.

In another embodiment off the present invention, the moisture barrier comprises an enteric and/or acrylic polymer, a plasticizer and a permeation enhancer and is present in a ratio of about 13:2:5. The enteric and/or acrylic polymer is preferably an acrylic polymer, which in turn is preferably a methacrylic acid copolymer available commercially as Eudragit® L 30 D-55. Although the amount of methacrylic acid copolymer present may vary from about 30% to about 90% by weight of the moisture barrier dry weight, it is preferable that the amount of the methacrylic acid copolymer is present at about 66% of the moisture barrier dry weight.

In another embodiment of the present invention, the plasticizer may be selected from the group consisting of polyols, organic esters, oils/glycerides and any combination thereof. The preferred plasticizer for use in the moisture barrier is a combination of a polyol and organic ester. The preferred polyol in the combination is polyethylene glycol 1450 with triethyl citrate being the preferred organic ester. The ratio of the organic ester to the polyol is preferably 1:2. It is preferable that the plasticizer be present from about 1% to about 30% and more preferably at about 10% by weight of the moisture barrier dry weight.

In another embodiment of the present invention, the permeation enhancer is a hydrophilic substance and may be selected from the group consisting of silicon dioxide, colloidal silicon, lactose, hydrophilic polymers, sodium chloride, aluminum oxide, colloidal aluminum oxide, silica, microcrystalline cellulose and any combination thereof. The permeation enhancer is preferably silicon dioxide and is present from about 20% to about 40% and more preferably at about 25% by weight of the moisture barrier dry weight.

In another embodiment of the present invention, the moisture barrier is applied such that the weight gained after application of the moisture barrier is no more than about 6% and preferably no more than about 2.5% of the tablet dry weight for both the 150 mg and 300 mg dose modified-release tablets of the invention.

In another embodiment of the present invention, the modified-release tablet of the invention provides for a stable bupropion hydrochloride formulation such that at least about 95% and preferably at least about 97.5% and even 98.5% or even 99% of the bupropion hydrochloride remains stable after about 12 months storage at 25° C.±2° C./60% RH±5% RH.

In another embodiment of the present invention, the modified-release tablet of the invention provides for a stable bupropion hydrochloride formulation such that at least about 95% and preferably at least about 97.5% and even 98.5% or even 99% of the bupropion hydrochloride remains stable after about 18 months storage at 25° C.±2° C./60% RH±5% RH In another embodiment of the present invention, the modified-release bupropion hydrochloride tablets of the invention are bioequivalent to either Wellbutrin® or Zyban®/Wellbutrin® SR tablets and do not exhibit a food effect.

In another aspect of the invention, the moisture barrier substantially impedes or retards the absorption of moisture into the tablet, thereby increasing the stability of the bupropion hydrochloride

BRIEF DESCRIPTION OF THE DRAWINGS

The present invention will be further understood from the following detailed description with reference to the following drawings in which.

DETAILED DESCRIPTION OF THE INVENTION

Figure 1A:
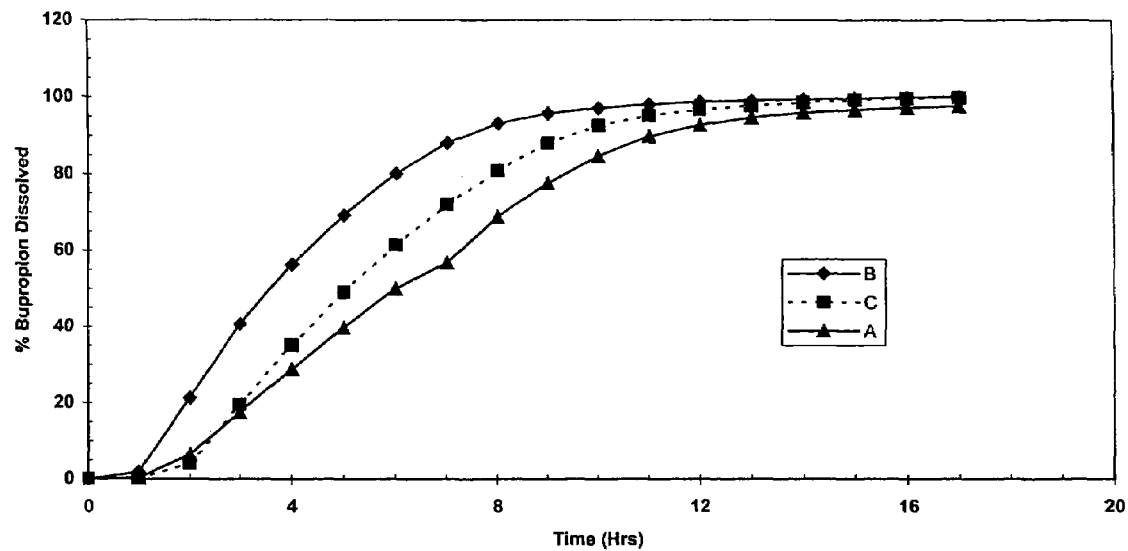
FIG. 1A is a graph illustrating the dissolution profile of a 150 mg dosage strength bupropion hydrochloride modified-release tablets with three different release rates according to an embodiment of the invention.

The invention described herein relates to a modified-release tablet having a core comprising a pharmaceutically acceptable salt of bupropion and conventional excipients, surrounded by a control-releasing coat, which controls the release of the pharmaceutically acceptable salt of bupropion, and a moisture barrier, which surrounds the control-releasing coat. The modified-release tablet of the invention is bioequivalent.

1. The Core

The core of the modified-release tablet comprises an effective amount of a pharmaceutically acceptable salt of bupropion, a binder, and a lubricant and may contain other conventional inert excipients. The amount of the active drug present may vary in an amount from about 50% to about 90% by weight of the tablet dry weight, and preferably from about 70% to about 90% by weight of the tablet dry weight. The pharmaceutically acceptable salt of bupropion is preferably bupropion hydrochloride. The tablet comprises an amount of bupropion hydrochloride that can vary from about 50 mg to about 450 mg. Preferably, the tablet comprises 150 mg or 300 mg of bupropion hydrochloride. For a 150 mg dose tablet the bupropion hydrochloride is about 78% by weight of the tablet dry weight. For the 300 mg dose, the amount of bupropion hydrochloride is present at about 83% by weight of the tablet dry weight. For both the 150 mg and 300 mg dose bupropion hydrochloride modified-release tablets of the invention, the amount of bupropion hydrochloride is present at about 94% by weight of the dry core for each dose.

A binder (also sometimes called adhesive) is added to a drug-filler mixture to ensure that granules and tablets can be formed with the required mechanical strength. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are generally considered the most effective, and this is therefore the most common way of incorporating a binder into granules. The binder used herein is in the form of a solution binder. Non-limiting examples of binders useful for the core include water-soluble polymers such as modified starch, gelatin, polyvinylpyrrolidone, cellulose derivatives (such as for example hydroxypropyl methylcellulose (HPMC) and hydroxypropyl cellulose (HPC)) and polyvinyl alcohol. The amount of binder present may vary from about 0.5% to about 15% by weight of the tablet dry weight, preferably from about 1% to about 6% by weight of the tablet dry weight, and most preferably about 3% by weight of the tablet dry weight. For both the 150 mg and 300 mg dose tablets, the amount of binder may be present preferably from about 1% to about 6% by weight of each dry core weight and more preferably at about 3% by weight of each dry core weight. The preferred binder is polyvinyl alcohol.

Lubricants are added to pharmaceutical formulations to ensure that tablet formation and ejection can occur with low friction between the solid and the die wall. High friction during tabletting can cause a series of problems, including inadequate tablet quality (capping or even fragmentation of tablets during ejection, and vertical scratches on tablet edges) and may even stop production. Accordingly, lubricants are added to almost all tablet formulations including the bupropion hydrochloride tablet formulation described herein. Non-limiting examples of lubricants useful for the core include glyceryl behenate, stearic acid, hydrogenated vegetable oils (such as hydrogenated cottonseed oil (Sterotex®), hydrogenated soybean oil (Sterotex® (HM) and hydrogenated soybean oil & castor wax (Sterotex® K), stearyl alcohol, leucine and polyethylene glycol (MW 4000 and higher). The lubricant is preferably glyceryl behenate. The amount lubricant present may vary from about 1% to about 5% by weight of the tablet dry weight, preferably from about 2% to about 3% by weight of the tablet dry weight, and most preferably about 2.5% by weight of the tablet dry weight. For the 150 mg and 300 mg dose modified-release tablets of the invention the lubricant is present at about 2.5% by weight of the tablet dry weight and preferably from about 1% to about 6% by weight of the dry core weight and more preferably at about 3% by weight of the dry core weight for both dosages.

At this stage, the core formulation is an immediate release formulation resulting in 100% dissolution of the bupropion hydrochloride within 1 hour (data not shown). Ideally the core comprises only an effective pharmaceutical amount of pharmaceutically acceptable salt of bupropion, a binder, preferably polyvinyl alcohol, and a lubricant, preferably glyceryl behenate. However, if necessary, additional inert excipients consistent with the objects of the invention may be added to the core formulation. The additional inert excipients may be added to facilitate the preparation and/or improve patient acceptability of the final modified-release bupropion hydrochloride dosage form as described herein. The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

It is preferred that the granules to be compressed to form the core of the modified-release tablet of the invention described herein be manufactured by the wet granulation process. Essentially, wet granulation involves agitation of a powder (the active drug) by convention in the presence of a liquid (the solution binder) followed by drying. For forming the granules, which are to be eventually compressed into the tablet cores, the bupropion hydrochloride is first granulated, preferably with a solution binder, in a granulator, preferably but not necessarily a fluidized bed granulator such as for example a fluidized bed granulator manufactured by Glatt (Germany) or Aeromatic (Switzerland). The binder, preferably polyvinyl alcohol, is first dissolved or dispersed in a suitable solvent, preferably water. The solution binder is then top sprayed onto the drug in a granulator, preferably a fluidized bed granulator. Alternatively, granulation can also be performed in a conventional or high shear mixer. If necessary, the additional inert excipients such as for example a filler can be mixed with the bupropion hydrochloride prior to the granulation step.

The granules formed are subsequently dried and then sieved prior to blending the granules with the lubricant. Preferably, the dried granules are sieved through a 1.4 mm mesh screen. The sieved granules are then blended with the lubricant, and if necessary, any other additional inert excipients, which may improve processing of the modified-release tablets of the invention. Blending of the granules with the lubricant, and if necessary, any additional inert excipients, such as for example a glidant, may be performed in a V-blender or any other suitable blending apparatus. Glidants improve the flowability of the powder. This is especially important during tablet production at high production speeds and during direct compaction. However, because the requirement for adequate flow is high, a glidant is often also added to a granulation before tabletting. The blended granules are subsequently pressed into tablets and are hereinafter referred to as tablet cores. Tablet cores can be obtained by the use of standard techniques and equipment well known to the skilled artisan. Ideally, but not necessarily, the tablet cores are obtained by a rotary press (also referred to as a multi-station press) fitted with suitable punches.

2. Tablet Coatings

The tablet cores are coated in two stages. The control-releasing coating is applied directly onto the surface of the tablet cores and functions to control the release of the pharmaceutically acceptable salt of bupropion. The moisture barrier is applied directly onto the surface of the control-releasing coat to impede or retard the absorption of moisture 2.1 The Control-Releasing Coat The control-releasing coat is a semi-permeable coat comprising a water-insoluble, water-permeable film-forming polymer, a plasticizer and a water-soluble polymer.

Non-limiting examples of water-insoluble, water-permeable film-forming polymers useful for the control-releasing coat include cellulose ethers, cellulose esters, and polyvinyl alcohol. The preferred water-insoluble, water-permeable film forming polymers are the ethyl celluloses, and can be selected from the group consisting of ethyl cellulose grade PR100, ethyl cellulose grade PR20 and any combination thereof. Ethyl cellulose grade PR 100 is the preferred water-insoluble, water-permeable film forming polymer. The amount of the water-insoluble water-permeable film-forming polymer may vary from about 1% to about 8% by weight of the tablet dry weight and preferably from about 2% to about 6% by weight of the tablet dry weight. For the 150 mg dose bupropion hydrochloride modified-release tablets of the invention, the amount of water-insoluble water permeable film-forming polymer may vary from about 3% to about 6% by weight of the tablet dry weight. Preferably, the amount of the water-insoluble water-permeable film-forming polymer is present at about 6.3% by weight of the tablet dry weight. With respect to the control-releasing coat itself, the amount of water-insoluble water-permeable film-forming polymer may vary from about 35% to about 60% and by weight of the control-releasing coat dry weight. Preferably, the amount of water-insoluble water-permeable polymer is present at about 50% by weight of the control-releasing coat dry weight. For the 300 mg dose bupropion hydrochloride modified-release tablet of the invention, the amount of water-insoluble water-permeable film-forming polymer may vary from about 2% to about 5% by weight of the tablet dry weight. Preferably, the amount of water-insoluble water-permeable film forming polymer is present at about 3.6% by weight of the tablet dry weight. With respect to the control-releasing coat itself, the water-insoluble water-permeable film-forming polymer is present at about 45% by weight of the control-releasing coat dry weight.

Plasticizers are generally added to film coating formulations to modify the physical properties of the polymer to make it more usable. The amount and choice of the plasticizer contributes to the hardness of a tablet and may even affect its dissolution or disintegration characteristics, as well as its physical and chemical stability. One important property of plasticizers is their ability to make a coat elastic and pliable, thereby decreasing the coat's brittleness. Non-limiting examples of plasticizers useful for the control-releasing coat described herein include polyols, such as polyethylene glycol of various molecular weights, organic esters, such as diethyl phthalate or triethyl citrate, and oils/glycerides such as fractionated coconut oil or castor oil. The amount of plasticizer for the control-releasing coat may vary in an amount from about 0.5% to about 2% by weight of the tablet dry weight. The preferred plasticizer is polyethylene glycol 1450. For the 150 mg dose bupropion hydrochloride modified-release tablet of the invention, the amount of plasticizer present in the control-releasing coat may vary from about 1% to about 1.5% by weight of the tablet dry weight. Preferably, the amount of plasticizer is present at about 1.5% by weight of the tablet dry weight. For the 300 mg dose bupropion hydrochloride modified-release tablet of the invention, the amount of plasticizer present may vary from about 0.5% to about 2% by weight of the tablet dry weight. For both the 150 mg and 300 mg dosage forms, the plasticizer is present preferably from about 6% to about 30% by weight of the control-releasing coat dry weight and more preferably at about 12% by weight of the control-releasing coat dry weight.

Non-limiting examples of water-soluble polymers useful for the control-releasing coat include polyvinylpyrrolidone, hydroxypropyl methylcellulose and hydroxypropyl cellulose. The preferred water-soluble polymer is polyvinylpyrrolidone the amount of which may vary from about 1.5% to about 6% by weight of the tablet dry weight. With respect to the control-releasing coat itself, the amount of water-soluble polymer present may vary from about 25% to about 55% by weight of the control-releasing coat dry weight. For the 150 mg dose of the bupropion hydrochloride modified-release tablet of the invention, the amount of water-soluble polymer present may vary from about 3% to about 5% by weight of the tablet dry weight or from about 25% to about 50% by weight of the control-releasing coat dry weight. For the 300 mg dose of the bupropion hydrochloride modified-release tablet of the invention, the amount of water-soluble polymer present may vary from about 2% to about 5% of the tablet dry weight and about 43% of the control-releasing coat dry weight.

The ratio of water-insoluble water-permeable film forming polymer:plasticizer:water-soluble polymer for the 150 mg dose of the modified-release bupropion hydrochloride tablet of the invention described herein may vary from about 3:1:4 to about 5:1:3. The preferred ratio is about 4:1:3. For the 300 mg dose of the modified-release bupropion hydrochloride tablet of the invention described herein, the ratio of the water-insoluble water-impermeable film-forming polymer:plasticizer:water-soluble polymer may vary from about 7:2:6 to about 19:5:18. The preferred ratio is about 13:4:12.

Generally, preparation and application of the control-releasing coat is as follows. The water-insoluble water-permeable film-forming polymer, preferably ethylcellulose, and the plasticizer, preferably polyethylene glycol 1450, are dissolved in an organic solvent such as a mixture of ethyl alcohol and isopropyl alcohol. The plasticizer, preferably polyvinyl pyrrolidone is next added until a homogenous mixture is achieved. The resulting control-releasing coat solution is then sprayed onto the tablet cores using a tablet coater, fluidized bed apparatus or any other suitable coating apparatus known in the art until the desired weight gain is achieved. The tablet cores coated with the control-releasing coat are subsequently dried before the moisture barrier is applied.

The skilled artisan will appreciate that controlling the permeability can control the release of the bupropion hydrochloride and/or the amount of coating applied to the tablet cores. The permeability of the control-releasing coat, can be altered by varying the ratio of the water-insoluble, water-permeable film-forming polymer:plasticizer:water-soluble polymer and/or the quantity of coating applied to the tablet core. A more extended release is generally obtained with a higher amount of water-insoluble, water-permeable film forming polymer. The addition of other excipients to the tablet core may also alter the permeability of the control-releasing coat. For example, if it is desired that the tablet core further comprise an expanding agent, the amount of plasticizer in the control-releasing coat should be increased to make the coat more pliable as the pressure exerted on a less pliable coat by the expanding agent would rupture the coat. Further, the proportion of the water-insoluble water-permeable film forming polymer and water-soluble polymer may also have to be altered depending on whether a faster or slower dissolution and/or release profile is desired.

Depending on the dissolution or in-vivo release profile desired the weight gained after coating the tablet core with the control-releasing coat might vary from about 3% to about 30% of the weight of the dry tablet core. For the 150 mg dose modified-release bupropion hydrochloride tablet of the invention the weight gain may vary from about 13% to about 16% of the weight of the dry tablet core. Preferably, the weight gain is about 15% of the weight of the dry tablet core. For the 300 mg dose modified-release bupropion hydrochloride tablet of the invention the weight gain may vary from about 8% to about 10% of the weight of the dry tablet core. Preferably, the weight gain is about 9% of the weight of the dry tablet core.

2.2 The Moisture Barrier

The moisture barrier is applied directly onto the control-releasing coat and comprises an enteric and/or an acrylic polymer, a permeation enhancer and optionally a plasticizer.

The enteric polymer is preferably an acrylic polymer. The acrylic polymer is preferably a methacrylic acid copolymer type C [poly(methacrylic acid, methyl methacrylate) 1:1] available commercially under the trade name Eudragit® (e.g. Eudragit L 30 D-55). The methacrylic acid copolymer is present in an amount, which may vary from about 1% to about 3% of the tablet dry weight and from about 55% to about 70% of the moisture barrier dry weight. For the 150 mg dose of the modified-release bupropion hydrochloride tablet of the invention, the methacrylic acid copolymer may vary from about 2% to about 3% of the tablet dry weight. Preferably, the amount of the methacrylic acid copolymer is present at about 2.5% of the tablet dry weight. With respect to the moisture barrier itself, the amount of the methacrylic acid copolymer is present preferably from about 30% to about 90% by weight of the moisture barrier dry weight and more preferably at about 66% of the moisture barrier dry weight. For the 300 mg dose of the modified-release bupropion hydrochloride tablet of the invention, the amount of the methacrylic acid copolymer may vary from about 1.5% to about 3% of the tablet dry weight. Preferably, the amount of methacrylic acid copolymer is present at about 2% by weight of the tablet dry weight. With respect to the coating itself, the methacrylic acid copolymer is present preferably from about 30% to about 90% of the moisture barrier dry weight and more preferably at about 66% of the moisture barrier dry weight for the 300 mg dose modified-release tablet of the invention.

It is known in the art that methacrylic acid copolymers tend to become brittle and therefore require a plasticizer. Non-limiting examples of plasticizers useful for the control-releasing coat described herein include polyols, such as polyethylene glycol of various molecular weights, organic esters, such as diethyl phthalate or triethyl citrate, and oils/glycerides such as fractionated coconut oil or castor oil. The preferred plasticizer comprises a combination of triethyl citrate and polyethylene glycol 1450. The ratio of triethyl citrate to polyethylene glycol 1450 is about 1:2. The plasticizer is present in an amount, which may vary from about 0.2% to about 0.5% and preferably from about 0.2% to about 0.4% of the tablet dry weight. The plasticizer is present at about 0.35% of the tablet dry weight for the 150 mg tablet and from about 0.2% to about 0:4% of the tablet dry weight for the 300 mg tablet.

With respect to moisture barrier itself, the plasticizer is present preferably from about 1% to about 30% by weight of the moisture barrier dry weight and more preferably at about 10% of the moisture barrier dry weight for both the 150 mg and 300 mg dose modified-release bupropion hydrochloride tablet of the invention. It is well known in the art that depending on the intended main function, excipients to be used in tablets are subcategorized into different groups. However, one excipient can affect the properties of a drug or the tablet as a whole in a series of ways, and many substances used in tablet formulations can therefore be described as multifunctional. Thus, the polyethylene glycol 1450 used in the plasticizer combination for the moisture barrier serves not only to increase the hydrophilicity of the moisture barrier, but also acts as a glidant.

In addition to the polyethylene glycol 1450, the permeation enhancer also acts as a glidant and also increases the hydrophilicity of the moisture barrier. The permeation enhancer is hydrophilic substance and may be selected from the group consisting of silicon dioxide, colloidal silicon, lactose, hydrophilic polymers, sodium chloride, aluminum oxide, colloidal aluminum oxide, silica, microcrystalline cellulose and any combination thereof. Silicon dioxide is the preferred permeation enhancer. The amount of permeation enhancer present may vary from about 0.5% to about 1% by weight of the tablet dry weight and is about 25% by weight of the moisture barrier dry weight. For the 150 mg dose modified-release bupropion hydrochloride tablet of the invention, the permeation enhancer is present in an amount of about 0.9% of the tablet dry weight and from about 20% to about 40% and preferably about 25% by weight of the moisture barrier dry weight. For the 300 mg dose modified-release bupropion hydrochloride tablet of the invention, the permeation enhancer is present in an amount, which may vary from about 0.5% to about 1% by weight of the tablet dry weight and is present preferably from about 20% to about 40% and preferably at about 25% by weight of the moisture barrier dry weight.

The ratio of the methacrylic acid copolymer:plasticizer: permeation enhancer is preferably about 13:2:5.

Generally, the preparation and application of the moisture barrier process is as follows. The plasticizer, preferably a combination of polyethylene glycol 1450 and triethyl citrate, is first added to water and the mixture mixed to homogeneity. The methacrylic acid co-polymer, preferably Eudragit® L 30 D-55, is next sieved and added to the plasticizer mixture and mixed to homogeneity. In a separate container the permeation enhancer, preferably silicon dioxide is dissolved in water until a homogeneous mixture is achieved. The plasticizer and methacrylic acid copolymer mixture is then combined with the permeation enhancer solution and mixed to homogeneity. The resulting moisture barrier solution is then sprayed onto the tablet cores coated with the control-releasing coat using a tablet coater, fluidized bed apparatus or any other suitable coating apparatus known in the art until the desired weight gain is achieved. The tablets coated with the moisture barrier are subsequently dried prior to packaging.

The moisture barrier is applied to the control-releasing coated tablet cores such that the weight gain is no more than about 6% and preferably no more than about 2.5% of the tablet dry weight of both the 150 mg and 300 mg modified-release bupropion hydrochloride tablets of the invention. The amount of the moisture barrier applied does not render the bupropion hydrochloride modified release tablet described herein resistant to gastric fluid and has no significant impact on the drug release characteristics.

The moisture barrier as used herein does not function as an enteric coat. Even though the methacrylic acid copolymer, Eudragit® L 30 D-55, is referenced and is used in enteric coating formulations in the art, its functionality is formulation dependent and on the quantity of the material applied. As is known in the art, an enteric coating is applied where a drug may be destroyed or inactivated by gastric juice or where the drug may irritate the gastric mucosa. To meet the requirements for an enteric coat, the test as described in the USP (method A or B) stipulates that after 2 hours in acidic media (0.1N HCl), no individual values of at least six experiments exceed 10% of the active drug dissolved and not less than 75% dissolved at 45 minutes in pH 6.8. The moisture barrier does not meet this requirement for the following reasons even though the bupropion hydrochloride is not negatively affected in acidic media nor is it irritating the gastric mucosa: (1) to obtain enteric integrity with a film containing Eudragit® L 30 D-55, a weight gain of between about 6% to about 8% based on the dry polymer per dosage unit is recommended. The amount of Eudragit® L 30 D-55 solid applied onto the control-releasing coated tablet cores is no more than 6% and preferably no more than 2.5%, (2) if enteric integrity would be required, the dissolution test for the finished product (i.e., the moisture barrier coated tablet cores) at the 2 hour time point would not stipulate a limit of no more than 20%, and (3) analytical tests performed on the final two coat product indicate that the product does not meet all the test requirements as an enteric coated product as defined by USP test methods. Since the moisture barrier is applied directly onto the control release coat, tests were conducted to determine if the moisture barrier applied directly onto the immediate release tablet cores function as an enteric coat. Tests show that after 1 hour more than 40% of the bupropion hydrochloride is released from the tablet cores in 0.1 N HCl and hence does not fall within the definition of the USP for an enteric coat (see Example 2). The functionality of the moisture barrier was also confirmed by determining the moisture content using the Karl-Fischer (KF) test of the individually coated control releasing and moisture barrier coated tablet cores under accelerated conditions (40° C.±2° C./75% RH±5% RH) in an open glass dish for 10 days (see Example 2). The results show that moisture content for the control-releasing coated tablet cores is higher than for the moisture barrier coated tablet cores. Cumulatively these data establish the functionality of the moisture barrier as a coat, which substantially impedes or retards the absorption of moisture and not as an enteric coat as defined by the USP.

The tablet of the invention provides for an extended-release of the bupropion hydrochloride though no pore forming agent is present in the formulation. The above formulation also provides for a stable bupropion hydrochloride formulation such that after about 2 hours, no more than about 20%, preferably about 2% to about 18%, more preferably about 4% to about 8%, and most preferably about 5% of the bupropion hydrochloride content is released, after about 4 hours, about 20% to about 45%, preferably about 21% to about 37%, more preferably about 28% to about 34%, and most preferably about 32% of the bupropion hydrochloride content is released, after about 8 hours, about 40% to about 90%, preferably about 60% to about 85%, more preferably about 68% to about 74%, and most preferably about 74% of the bupropion hydrochloride content is released and after about 16 hours no less than about 80%, preferably no less than about 93%, more preferably no less than about 96%, and most preferably no less than about 99% of the bupropion hydrochloride content is released.

The positive impact on stability of the modified-release bupropion hydrochloride tablet of the formulation described herein is evident in the tests performed to evaluate the total impurities present in either the 150 mg or 300 mg dosage forms through 6 months under accelerated conditions (40° C.±2° C./75% RH±5% RH) as well as through 12 months and 18 months of long-term stability at 25° C.±2° C./60% RH±5% RH. The stability tests showed reduced values (relative to Wellbutrin SR) in total impurities in tablets.

In 7 count, 40 cc and 30 count, 100 cc HDPE bottles for both the 150 mg and 300 mg dosage strength modified-release tablets of the invention for example, the total impurities present should be no more than about 2.5% by weight of the amount of bupropion hydrochloride in the tablet, preferably no more that about 1.5%, and most preferably no more that about 0.6% through at least 12 months of long-term stability at 25° C.+2° C./60% RH±5% RH. At 18 months of long-term-stability at 25° C.±2° C./60% RH±5% RH, the total impurities present should be no more than about 2.5% by weight of the amount of bupropion hydrochloride in the tablet, preferably no more than about 1.5%, and most preferably no more than about 0.7% by weight of the amount of bupropion hydrochloride in the tablet. Thus, the modified-release bupropion hydrochloride tablet according to the present invention contains at least about 95% w/w and more preferably at least 98% or even at least 99% of undegraded bupropion hydrochloride after storage for 12 or 18 months of long-term stability under the humidity and temperature conditions usually encountered in pharmacies and medicine cabinets i.e. room temperature and 35-60% humidity. Thus, when used in a pharmaceutical preparation for example, a tablet, it will still retain at least 95% of its potency and preferably at least 98% or even 99% of its potency after one year of storage at room temperature (15°-25° C.) at 35-60% humidity. For example if the tablet initially contains 300 mg bupropion hydrochloride (labeled amount) at time of preparation, after one-year storage at least 285 mg of bupropion hydrochloride and preferably at least 294 mg or more will remain in the tablet.

The KF moisture content and the total amount of impurities of bupropion hydrochloride for the 150 mg dosage strength tablets of the invention when stored under accelerated conditions through at least 6 months for the 7 count, 40 cc HDPE bottle configurations should be no more than about 1%. The same bottle and tablet configuration for the 300 mg dosage strength stored under the same accelerated conditions should have a KF moisture content of no more than about 1% and total impurities of no more than about 0.6% through at least 6 months. The 150 mg tablets stored in the 30 count, 100 cc HDPE bottle configuration should have a KF moisture content of no more than about 1% and total impurities of no more than about 1.2% when stored under accelerated conditions through at least 6 months. The 300 mg dosage strength tablets stored in the same configuration under the same conditions for the same amount of time should have a KF moisture content of no more than about 1% and total impurities of no more than about 0.8%. When stored in an open glass dish, the KF moisture content of a 300 mg dosage strength modified-release tablet of the invention should be no more than about 0.8% after 3 days and preferably no more than 0.45% after 10 days when stored under accelerated conditions. When stored in tightly sealed glass bottles the KF moisture content should be no more than 0.45% after 3-days and preferably no more than about 0.4% after 10 days.

The following examples illustrate the present invention and are not intended to limit the scope of the present invention.

EXAMPLE 1

1. Modified Release Tablet Formulations

Three different core formulations were prepared for each of the 150 mg and 300 mg modified release bupropion hydrochloride tablets as shown in Table 1:

TABLE 1

CORE FORMULATION

| Ingredients | 150 mg | | | 300 mg | | |
| --- | --- | --- | --- | --- | --- | --- |
| | A (mg/%)[1] | B (mg/%) | C (mg/%) | A' (mg/%) | B' (mg/%) | C' (mg/%) |
| Bupropion hydrochloride | 150/81.1 | 150/82.4 | 150/79 | 300/79 | 300/87.6 | 300/83.5 |
| Binder[2] | 5.3/2.86 | 5.3/2.9 | 5.3/2.8 | 10.6/2.8 | 10.6/3.1 | 10.6/2.95 |
| Lubricant[3] | 4.7/2.54 | 4.7/2.58 | 4.7/2.46 | 9.4/2.48 | 9.4/2.74 | 9.4/2.61 |
| Purified water[4] | * | * | * | * | * | * |
| Total dry weight of core | 160/86.48 | 160/87.91 | 160/83.77 | 320/84.43 | 320/93.47 | 320/89.02 |

[1]The mg/% values represent the proportion of the ingredient in relation to the tablet dry weight
[2]Polyvinyl alcohol
[3]Glyceryl behenate (Compritol 888 ATO)
[4]Evaporated during drying The water is first heated to 60±5° C. The binder (polyvinyl alcohol) is next dissolved in the water to homogeneity and then passed through a 0.7 mm mesh screen and allowed to cool to a temperature of no more than about 30° C. Bupropion hydrochloride is placed in the top spraying chamber of a fluidized bed apparatus, such as for example a Glatt GPCG1 fluidized bed apparatus. The solution binder (i.e., the polyvinyl alcohol solution) is sprayed onto the bupropion hydrochloride, with the in-process parameters shown in Table 2:

TABLE 2

GRANULATION PROCESS PARAMETERS

| Air flow (m³/h) | 2000-2500 |
| --- | --- |
| Pump flow rate (g/min) | 150-250 |
| Inlet temperature | 50° C.-70° C. |
| Outlet temperature | 30° C.-50° C. |
| Spraying pressure (Bar) | 3-5 |
| Product temperature | 35° C.-50° C. |

Once the granulation is completed, the granules are allowed to dry and then cooled to a temperature of no more than about 35° C. The bupropion hydrochloride granules are then passed through a 1.4 mm mesh sieve.

The lubricant (glyceryl behenate) together with the sieved granules is then blended in a V-Blender until the mixture is uniformly mixed. The resulting mixture is pressed into tablet cores using a rotary tablet press (Manesty Unipress) with an average hardness from about 8 Sc to about 25 Sc and an average thickness from about 3.9 mm to about 4.5 mm for the 150 mg tablet cores, and an average hardness from about 12 Sc to about 33 Sc, and an average thickness from about 4.8 mm to about 5.4 mm for the 300 mg tablet cores. The friability of the tablet cores for both dosage strengths is no more than 0.8%. The tablet cores are then coated with the control-releasing coat formulations shown in Table 3:

TABLE 3

CONTROL-RELEASING COAT FORMULATION

| Ingredients | 150 mg | | | 300 mg | | |
| --- | --- | --- | --- | --- | --- | --- |
| | A (mg/%[1]) | B (mg/%) | C (mg/%) | A' (mg/%) | B' (mg/%) | C' (mg/%) |
| Water-insoluble water-permeable film forming polymer[2] | 10.26/5.55 | 5.63/3.1 | 12/6.28 | 19/5.01 | 6.71/1.96 | 13.05/3.63 |
| Water soluble polymer[3] | 5.64/3.05 | 7.5/4.1 | 9/4.7 | 18.06/4.77 | 6.37/1.86 | 12.40/3.45 |
| Plasticizer[4] | 2.1/1.14 | 1.88/1.03 | 3/1.6 | 5.16/1.36 | 1.82/0.53 | 3.55/0.99 |
| Denatured Ethyl Alcohol 95%[5] | * | * | * | * | * | * |
| Isopropyl Alcohol 99%[5] | * | * | * | * | * | * |
| Dry weight of control-releasing coat | 18/9.73 | 15/8.24 | 24/12.56 | 42.22/11.14 | 14.9/4.35 | 29/8.07 |

[1]The % values represent the proportion of the ingredient in relation to the tablet dry weight
[2]Ethylcellulose 100 (Ethocel ®)
[3]Polyvinylpyrrolidone (Kollidon ® 90F)
[4]Polyethylene Glycol 1450 (Carbowax ®)
[5]Evaporated during drying The plasticizer (polyethylene glycol 1450) followed by the water-insoluble water permeable film-forming polymer (ethylcellulose 100) is added to a portion of a mixture of the denatured ethyl alcohol and the isopropyl alcohol. Once mixed, the water-soluble polymer is gradually added to the above mixture to avoid large particles or clumping. The solution is mixed to homogeneity. The remainder of the denatured ethyl alcohol and isopropyl alcohol is then added to the coating mixture and mixing is continued until a homogeneous solution is achieved. The coating solution is then passed through a DeBee Homogenizer (nozzle size 7, process pressure at 8500±2000 psi and back pressure at 1000±250 psi). The homogenized coating solution is then sprayed onto the tablet cores in a tablet coater (O'Hara 36 Side Vent) with the process parameters shown in Table 4:

TABLE 4

CONTROL-RELEASING COAT PROCESS PARAMETERS

| Process Parameters | 150 mg tablet cores | 300 mg tablet cores |
|---|---|---|
| Pan Speed (rpm) | 5-15 | 5-15 |
| Exhaust Air Temperature (° C.) | 25 ± 40 | 25 ± 40 |
| Inlet Air Temperature (° C.) | 300 ± 60 | 30 ± 60 |
| Spray Rate (g/min) | 160-400 | 160-400 |
| Atomizing Air Pressure (psi) | 30-50 | 30-50 |
| Pattern Air Pressure (psi) | 20-40 | 20-40 |
| Air Flow (CFM) | 800-1100 | 800-1100 |

Coating of the tablet cores with the control-releasing coat solution is continued until a weight gain of about 24 mg (wet coating range of about 22 to about 26 mg) and a weight gain of about 29 mg (wet coating range of about 27 to about 31 mg) is achieved for the 150 mg and 300 mg tablet cores respectively. Once the desired weight gain is reached, the coating is stopped and the coated tablet cores are dried at an inlet air temperature of about 35±2° C. with a pan speed set at about 2 rpm. The dried and cooled coated tablet cores are next coated with the moisture barrier formulation shown in Table 5:

The plasticizer combination, preferably polyethylene glycol 1450 and triethyl citrate, are first dissolved in a portion of the purified water and mixed to homogeneity. While the plasticizer solution is being mixed, the methacrylic acid copolymer, preferably Eudragit® L 30 D-55, is passed through a 0.3 mm mesh screen in a separate container. The plasticizer solution is next added to the methacrylic acid copolymer and mixed until a homogenous solution is achieved. While the methacrylic acid copolymer/plasticizer solution is being mixed, the permeation enhancer, preferably, silicon dioxide, is dissolved in the remainder of the water and mixed with a high shear mixer until the suspension is homogenous. The final moisture barrier solution is obtained by mixing the permeation enhancer solution with the methacrylic acid copolymer/plasticizer mixture. The homogenized moisture barrier solution is then sprayed onto the control release coated tablet cores in a coating pan with the process parameters as shown in Table 6:

TABLE 6

MOISTURE BARRIER PROCESS PARAMETERS

| Process Parameters | 150 mg tablet cores | 300 mg tablet cores |
|---|---|---|
| Pan Speed (rpm) | 5-15 | 5-15 |
| Exhaust Air Temperature (° C.) | 25-40 | 25-40 |
| Inlet Air Temperature (° C.) | 30-60 | 30-60 |
| Spray Rate (g/min) | 160-400 | 160-400 |
| Atomizing Air Pressure (psi) | 30-50 | 30-50 |
| Pattern Air Pressure (psi) | 20-40 | 20-40 |
| Air Flow (CFM) | 800-1100 | 800-1100 |

The moisture barrier is applied until a weight gain of about 7 mg (wet coating tablet range of about 6.3 to about 7.7 mg) and about 10.5 mg (wet coating tablet range of about 9.5-11.5 mg) is achieved for the 150 mg and 300 mg dose modified release tablets respectively. Once the desired weight gain is

TABLE 5

MOISTURE BARRIER FORMULATION

| Ingredients | 150 mg | | | 300 mg | | |
|---|---|---|---|---|---|---|
| | A (mg/%)[1] | B (mg/%) | C (mg/%) | A' (mg/%) | B' (mg/%) | C' (mg/%) |
| Methacrylic Acid Co-Polymer[2] | 4.59/2.48 | 4.59/2.52 | 4.59/2.40 | 10.99/2.9 | 4.88/1.42 | 6.86/1.91 |
| Plasticizer Combination (D + E)[3] | (D = 0.46 E = 0.23) 0.69/0.38 | (D = 0.46 E = 0.23) 0.69/0.38 | (D = 0.46 E = 0.23) 0.69/0.36 | (D = 1.1 E = 0.56) 1.66/0.44 | (D = 0.49 E = 0.25) 0.74/0.21 | (D = 0.69 E = 0.35) 1.04/0.29 |
| Permeation enhancer[4] | 1.72/0.93 | 1.72/0.95 | 1.72/0.90 | 4.11/1.08 | 1.83/0.53 | 2.57/0.71 |
| Purified Water[5] | * | * | * | * | * | * |
| Dry weight of moisture barrier | 7/3.78 | 7/3.85 | 7/3.66 | 16.76/4.42 | 7.45/2.18 | 10.47/2.91 |

[1]The mg/% values represent the total proportion of the ingredient in relation to the tablet dry weight
[2]poly(methacrylic acid, methyl methacrylate) 1:1 (Eudragit ® L 30 D-55)
[3]D = Polyethylene Glycol 1450 (Carbowax ®), E = Triethyl Citrate
[4]Silicon Dioxide (Syloid ® 244)
[5]Evaporated during drying reached, the coating is stopped and the coated tablets are dried at an inlet air temperature of about 35±2° C. with a pan speed set at about 2 rpm.

The coated tablets are finally printed with suitable indicia using suitable black ink, such as for example Opacodeg S-1-8090 black ink, using a tablet printer (Print International).

The dissolution profile for each of the three 150 mg and 300 mg doses was determined under the following dissolution conditions:

Medium: 900 ml, 0.1N HCl
Method: USP Type I Apparatus (150 mg dose)/USP Type II Apparatus (300 mg dose), at 75 rpm and 37° C.

2. Stability of the Modified Release Tablet Formulations

The formulations are free of a stabilizer. To determine the stability of the bupropion hydrochloride in the absence of stabilizer, stability tests were conducted both under accelerated conditions over 6 months at 40° C.±2° C./75% RH±5% RH and under long-term conditions over 12 and 18 months at 25° C.±2° C./60% RH±5% RH. At the end of the specified time period, the tablets were analyzed for impurities resulting from the degradation of bupropion hydrochloride by HPLC. The degradation products included those listed in the USP (26$^{th}$ edition, pg 281) and any other peaks that appeared on the chromatogram. The results of the stability analysis under both accelerated and long-term condition for both the 150 mg and 300 mg dosage forms is shown in Tables 8, 9 and 10:

TABLE 8

| | Accelerated Conditions (40° C. ± 2° C./75 ± 5% RH) | | | | | | | |
|---|---|---|---|---|---|---|---|---|
| | 150 mg[1] | | | | 300 mg[1] | | | |
| Time (months) | Moisture[2] | Total Impurities[3] | Moisture[2] | Total Impurities[3] | Moisture[2] | Total Impurities[3] | Moisture[2] | Total Impurities[3] |
| 1 | 0.67 | 0.63 | 0.93 | 0.63 | 0.7 | 0.50 | 0.57 | 0.63 |
| 3 | 0.6 | 0.80 | 0.8 | 0.86 | 0.7 | 0.70 | 0.67 | 0.84 |
| 6 | 1.0 | 1.09 | 1.0 | 1.22 | 1.0 | 0.98 | 0.9 | 1.20 |

[1]Moisture and Impurity values are an average of three lots
[2]KF Moisture content (%)
[3]Total impurities derived from break down of bupropion hydrochloride as a % of bupropion hydrochloride present at start of analysis The results are presented in Table 7 as the mean percent release of the total bupropion hydrochloride content in the coated tablets:

TABLE 7

| Time | 150 mg | | | 300 mg | | |
|---|---|---|---|---|---|---|
| (Hrs) | B | C | A | B' | C' | A' |
| 0 | 0 | 0 | 0 | 0 | 0 | 0 |
| 1 | 1.7 | 0.1 | 0.3 | 15 | 1 | 0.15 |
| 2 | 21.2 | 4.2 | 6.4 | 33 | 9.5 | 3.5 |
| 3 | 40.6 | 19.5 | 17.5 | 48.5 | 23.5 | 11.5 |
| 4 | 56.2 | 35.1 | 28.7 | 62.5 | 36.5 | 20 |
| 5 | 69.2 | 49 | 39.7 | 73.5 | 48 | 29 |
| 6 | 80.1 | 61.4 | 49.9 | 83 | 58.5 | 38 |
| 7 | 88.1 | 72 | 56.7 | 90 | 67.5 | 46 |
| 8 | 93.1 | 80.9 | 68.7 | 94.5 | 75.5 | 54 |
| 9 | 95.7 | 88.1 | 77.6 | 97 | 82 | 62 |
| 10 | 97.1 | 92.6 | 84.6 | 98 | 87 | 69.5 |
| 11 | 98 | 95.1 | 89.7 | 99 | 90.5 | 76.5 |
| 12 | 98.7 | 96.7 | 92.7 | 99.5 | 93.5 | 82.5 |
| 13 | 99 | 97.7 | 94.6 | 100 | 95 | 87 |
| 14 | 99.4 | 98.6 | 95.9 | 100 | 96 | 91 |
| 15 | 99.6 | 99.2 | 96.6 | 100.5 | 96.5 | 93.5 |
| 16 | 99.9 | 99.6 | 97.2 | 100.5 | 97.5 | 95 |
| 17 | 100 | 99.9 | 97.6 | 100.5 | 98 | 96.5 |
| | | | | 100.5 | 99 | 97 |
| | | | | 101 | 99 | 97.5 |
| | | | | 101 | 99 | 98.5 |
| | | | | 101 | 100 | 98.5 |
| | | | | 101 | 100 | 99 |
| | | | | 101 | 99.5 | 99.5 |
| | | | | 101 | 100 | 99.5 |

Figure 1B:
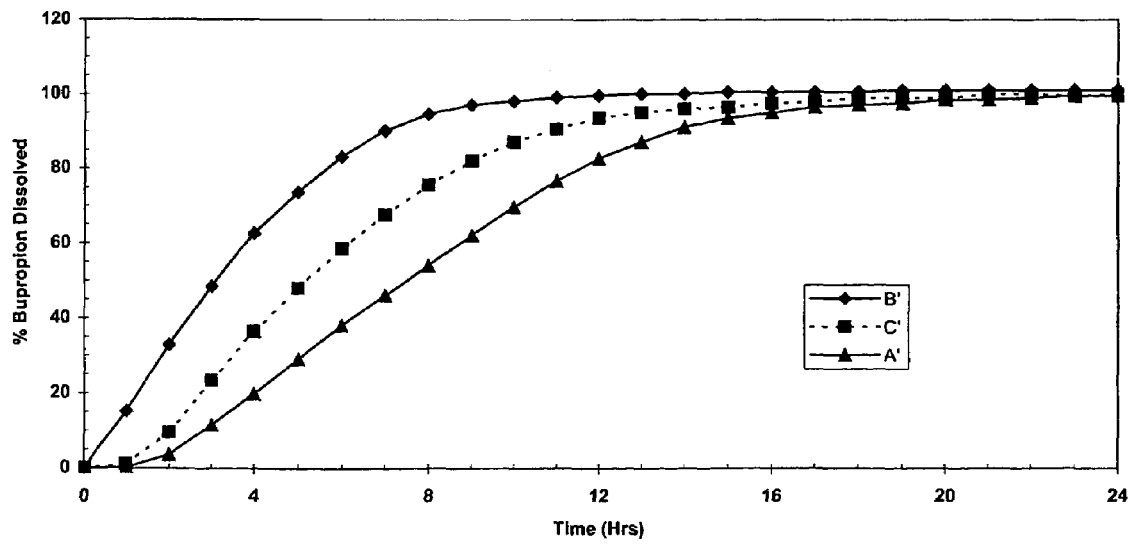
FIG. 1B is a graph illustrating the dissolution profile of a 300 mg dosage strength bupropion hydrochloride modified-release tablets with three different release rates according to an embodiment of the invention.

The mean dissolution profile for the three different 150 mg and 300 mg modified release bupropion hydrochloride tablets is shown in FIGS. 1A and 1B respectively. Formulation C and C' for the 150 mg and 300 mg dosage forms were selected for all further tests and manufacturing.

TABLE 9

| 12 months of long-term stability (25° C. ± 2° C./60% RH ± 5% RH) | | |
|---|---|---|
| Acceptable Limits | Data Derived | Amt. in Tablets at 12 months |
| Total Impurities 2.5% | 1.5% | 0.56% |

TABLE 10

| 18 months of long-term stability (25° C. ± 2° C./60% RH ± 5% RH) | | |
|---|---|---|
| Acceptable Limits | Data Derived | Amt. in Tablets at 18 months |
| Total Impurities 2.5% | 1.5% | 0.65% |

Figure 2A:
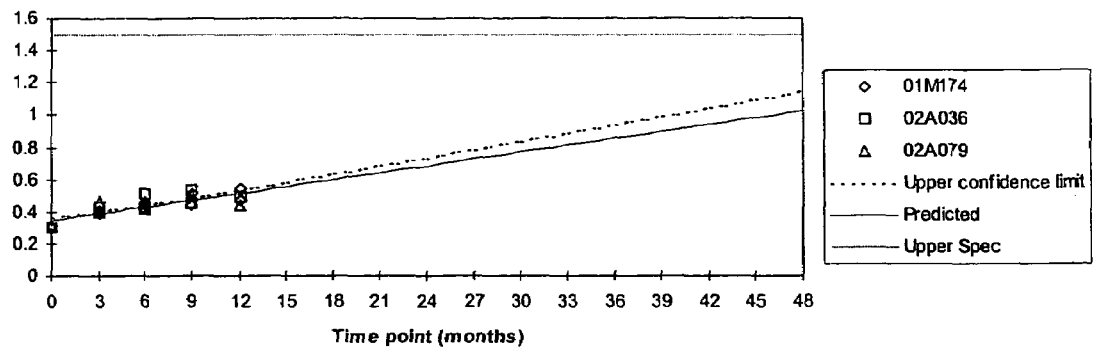
FIG. 2A is a graph illustrating the statistical analysis for Relative Response Factors (RRF) corrected total impurities content in the 150 mg dosage strength bupropion hydrochloride modified-release tablets according to an embodiment of the invention stored at 25° C.±2° C./60% RH±5% RH in HDPE bottles (7 ct, 40 cc and 30 ct, 100 cc).
Figure 2B:
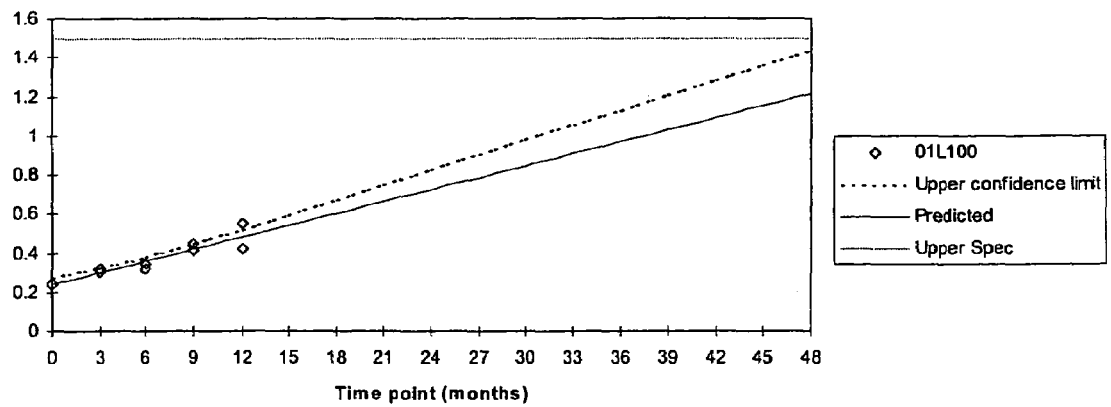
FIG. 2B is a graph illustrating the statistical analysis for Relative Response Factors (RRF) corrected total impurities content in the 300 mg dosage strength bupropion hydrochloride modified-release tablets according to an embodiment of the invention stored at 25° C.±2° C./60% RH±5% RH in HDPE bottles (7 ct, 40 cc and 30 ct, 100 cc).
Figure 3A:
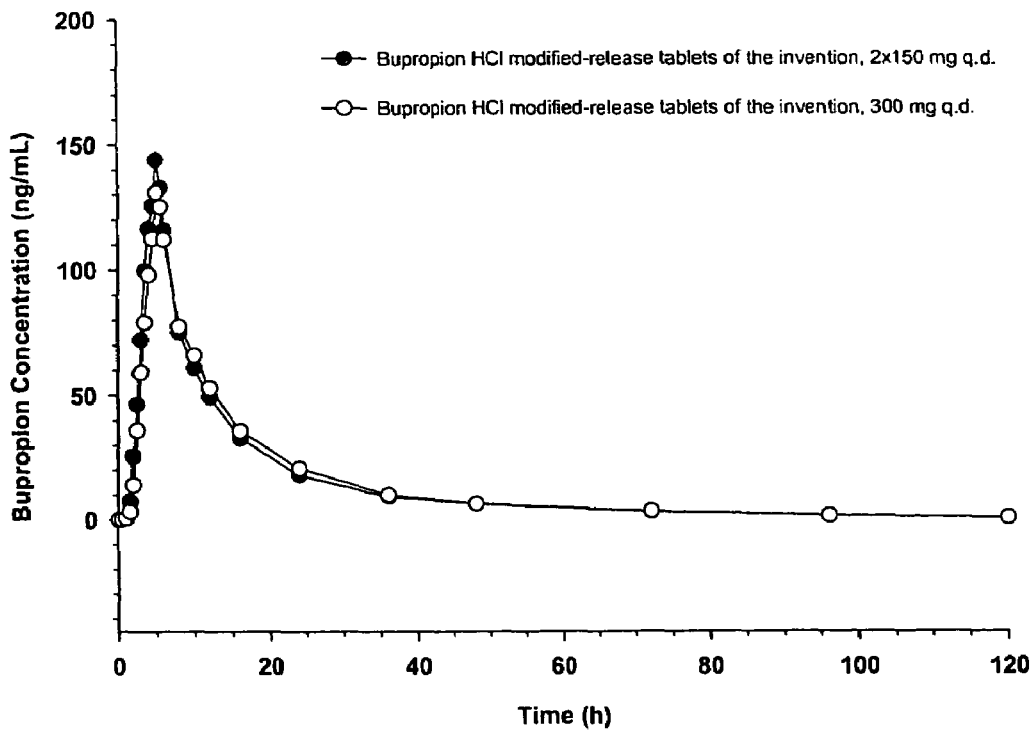
FIG. 3A is a graph illustrating the mean plasma bupropion concentrations of a dosage strength equivalency study after administration of 2×150 mg (q.d.) and 1×300 mg (q.d.) dosage strength modified-release bupropion hydrochloride tablets according to an embodiment of the invention.
Figure 3B:
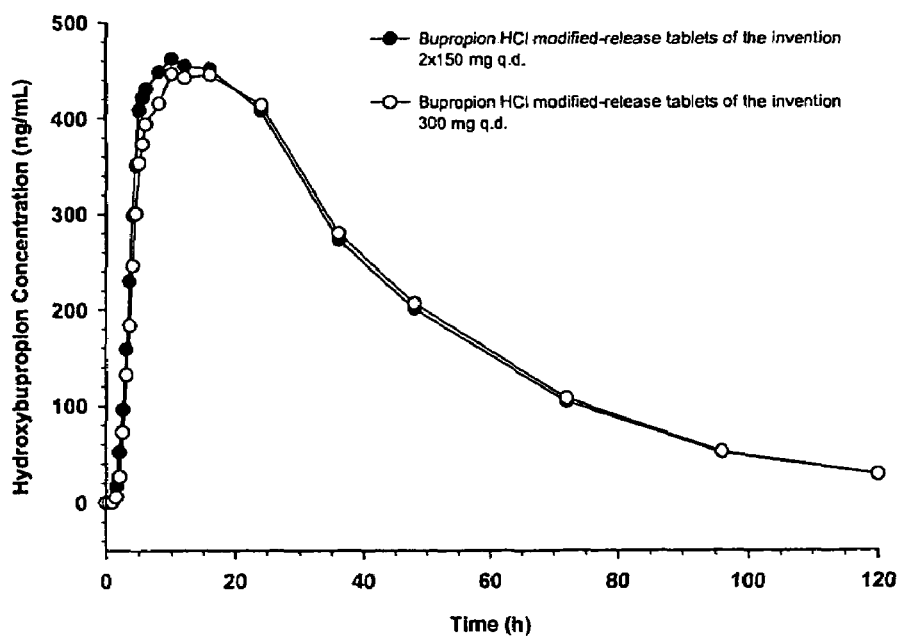
FIG. 3B is a graph illustrating the mean plasma hydroxybupropion concentrations of a dosage strength equivalency study after administration of 2×150 mg (q.d.) and 1×300 mg (q.d.) dosage strength modified-release bupropion hydrochloride tablets according to an embodiment of the invention.
Figure 3C:
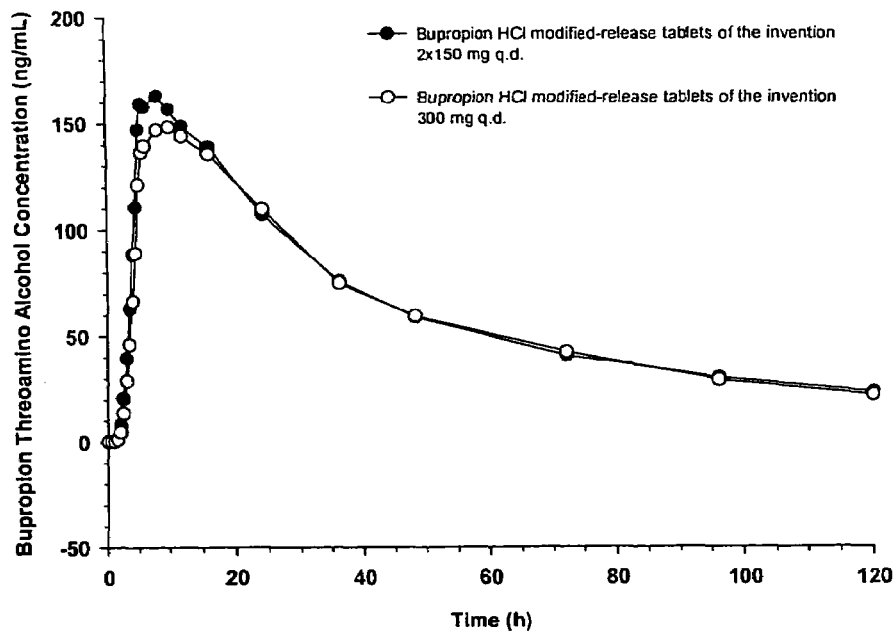
FIG. 3C is a graph illustrating the mean plasma bupropion threoamino alcohol concentrations of a dosage strength equivalency study after administration of 2×150 mg (q.d.) and 1×300 mg (q.d.) dosage strength modified-release bupropion hydrochloride tablets according to an embodiment of the invention.
Figure 3D:
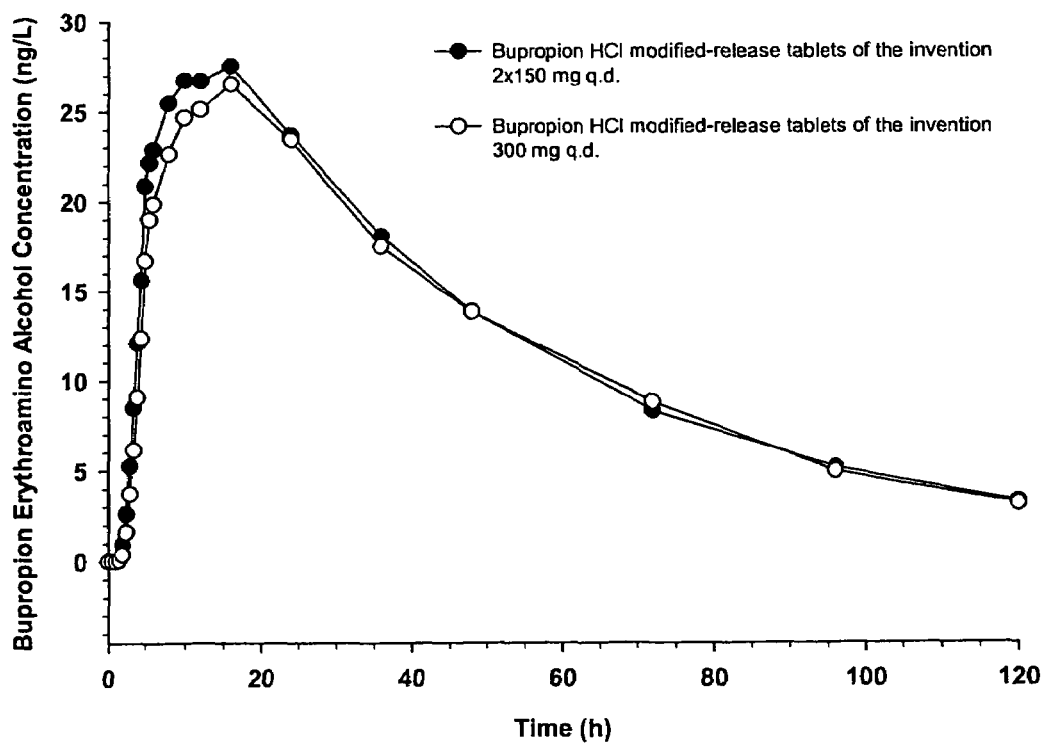
FIG. 3D is a graph illustrating the mean plasma bupropion erythroamino alcohol concentrations of a dosage strength equivalency study after administration of 2×150 mg (q.d.) and 1×300 mg (q.d.) dosage strength modified-release bupropion hydrochloride tablets according to an embodiment of the invention.
Figure 4A:
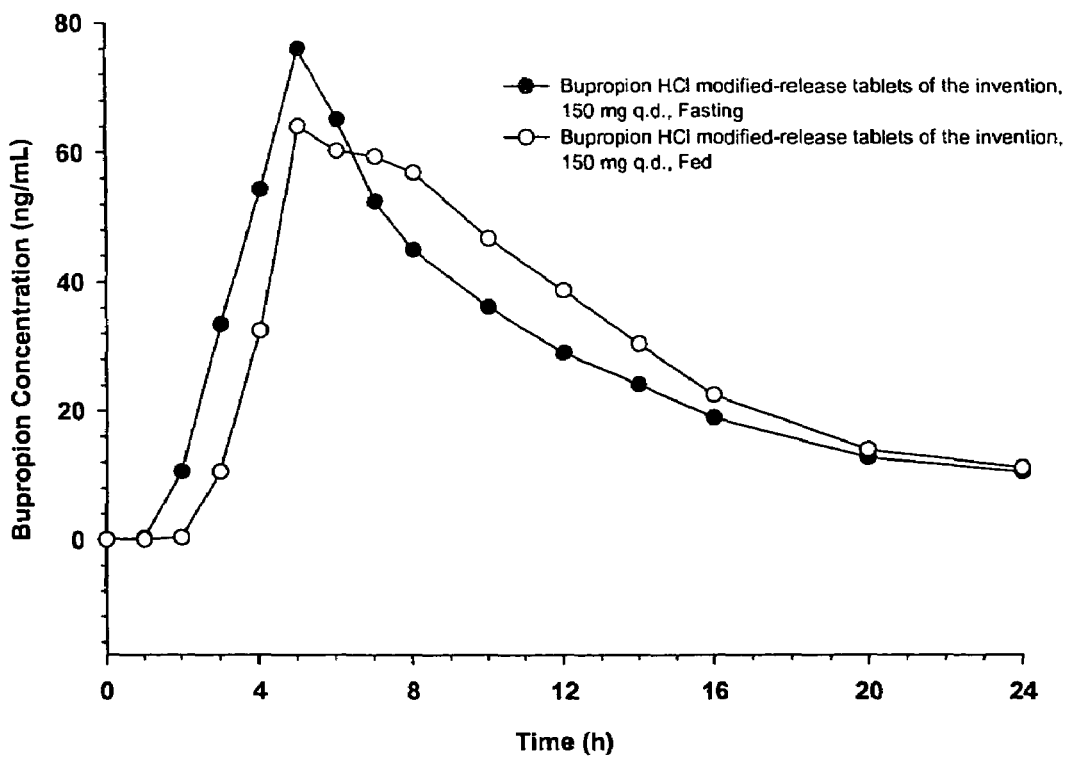
FIG. 4A is a graph illustrating the effect of food on the mean plasma bupropion concentrations after a single dose administration of a 150 mg dosage strength modified-release bupropion hydrochloride tablet according to an embodiment of the invention.
Figure 4B:
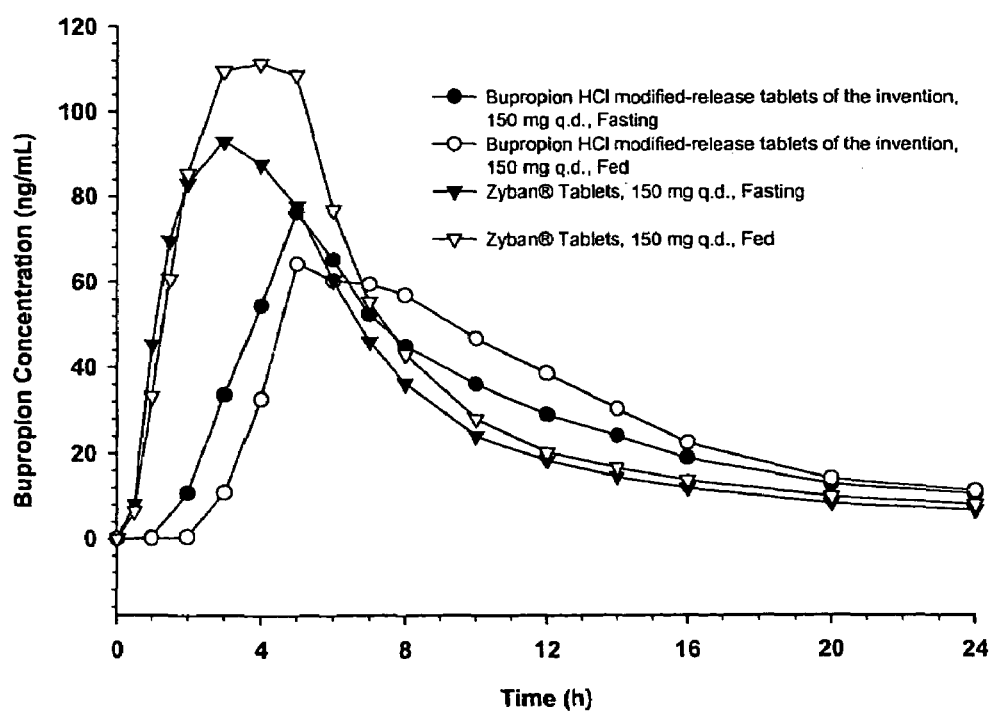
FIG. 4B is a graph comparing the mean plasma bupropion concentrations shown in FIG. 4A with the mean plasma bupropion concentrations after a single dose administration of the prior art 150 mg Zyban® tablet.
Figure 4C:
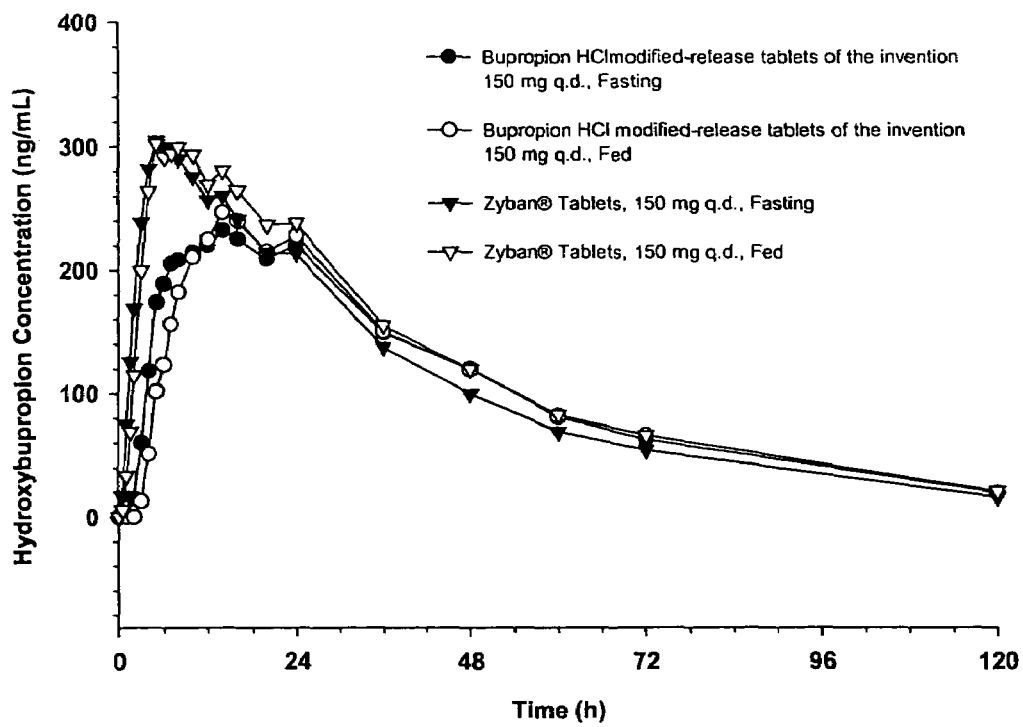
FIG. 4C is a graph comparing the mean plasma hydroxybupropion concentrations after a single dose administration of a 150 mg dosage strength modified-release bupropion hydrochloride tablet according to an embodiment of the invention with the mean plasma hydroxybupropion concentrations after a single dose administration of the prior art 150 mg Zyban® tablet.
Figure 4D:
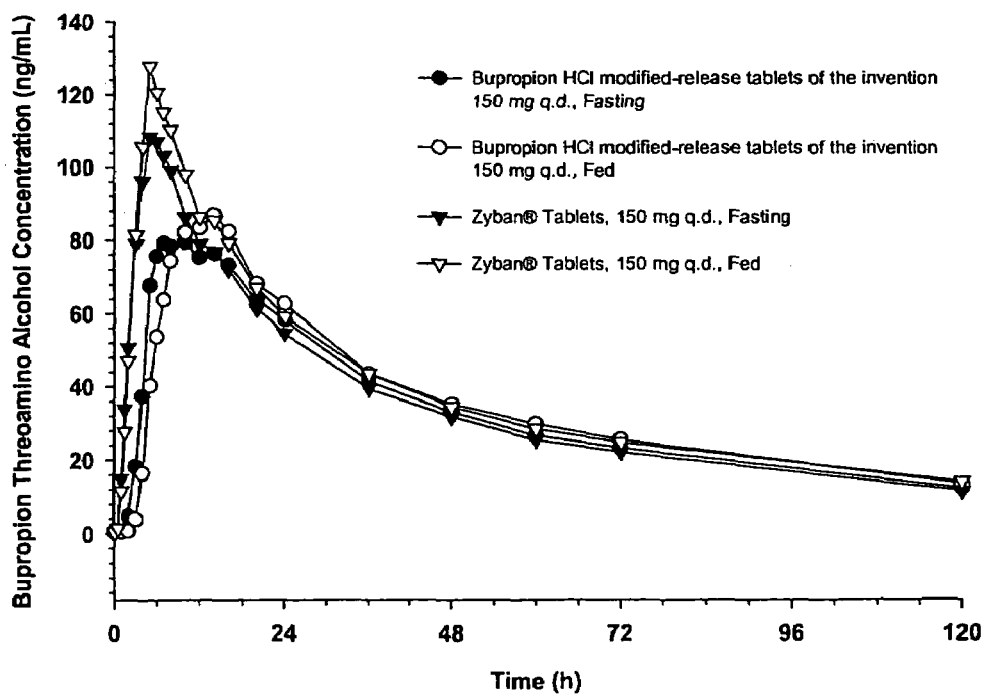
FIG. 4D is a graph comparing the mean plasma bupropion threoamino alcohol concentrations after a single dose administration of a 150 mg dosage strength modified-release bupropion hydrochloride tablet according to an embodiment of the invention with the mean plasma hydroxybupropion concentrations after a single dose administration of the prior art 150 mg Zyban® tablet.
Figure 4E:
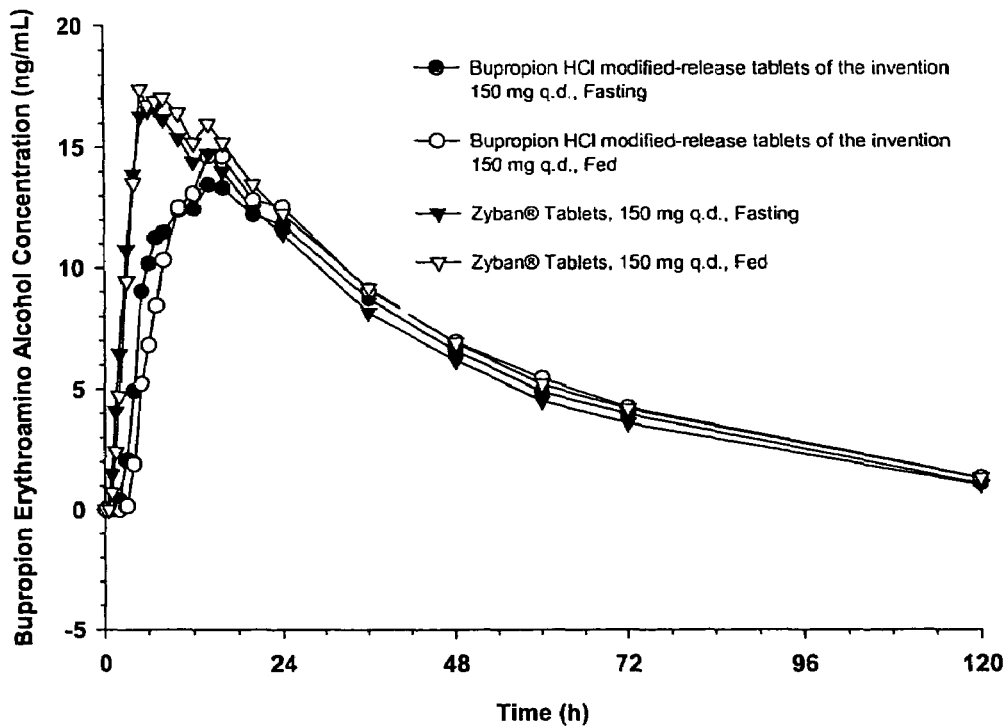
FIG. 4E is a graph comparing the mean plasma bupropion erythroamino alcohol concentrations after a single dose administration of a 150 mg dosage strength modified-release bupropion hydrochloride tablet according to an embodiment of the invention with the mean plasma hydroxybupropion concentrations after a single dose administration of the prior art 150 mg Zyban® tablet.
Figure 5A:
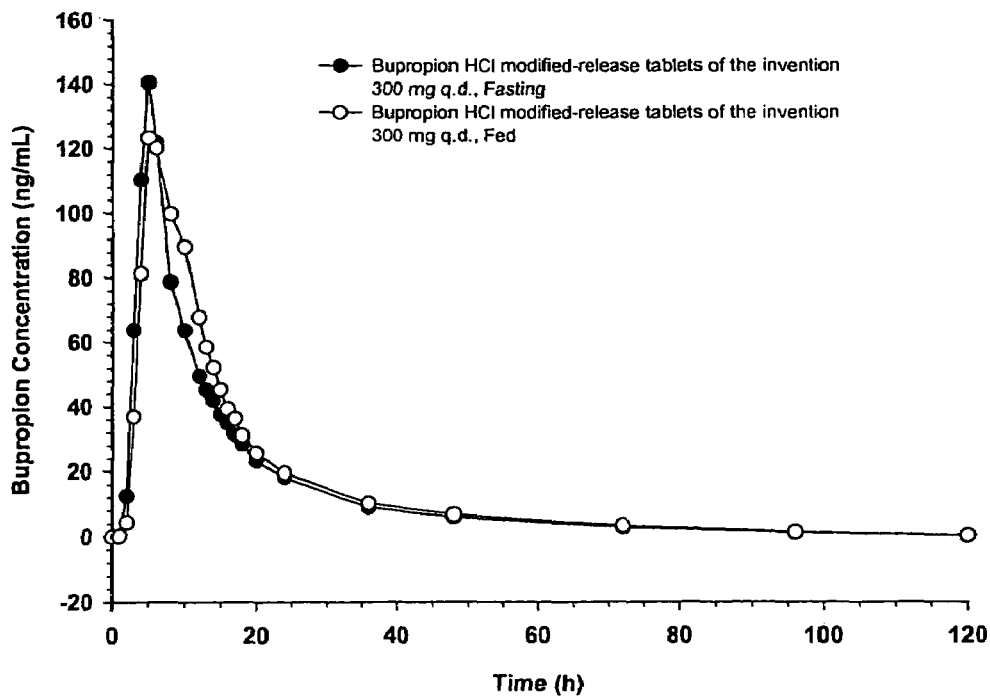
FIG. 5A is a graph comparing the effect of food on the mean plasma bupropion concentrations of a single dose once-daily 300 mg dosage strength modified-release bupropion hydrochloride tablet according to an embodiment of the invention.
Figure 5B:
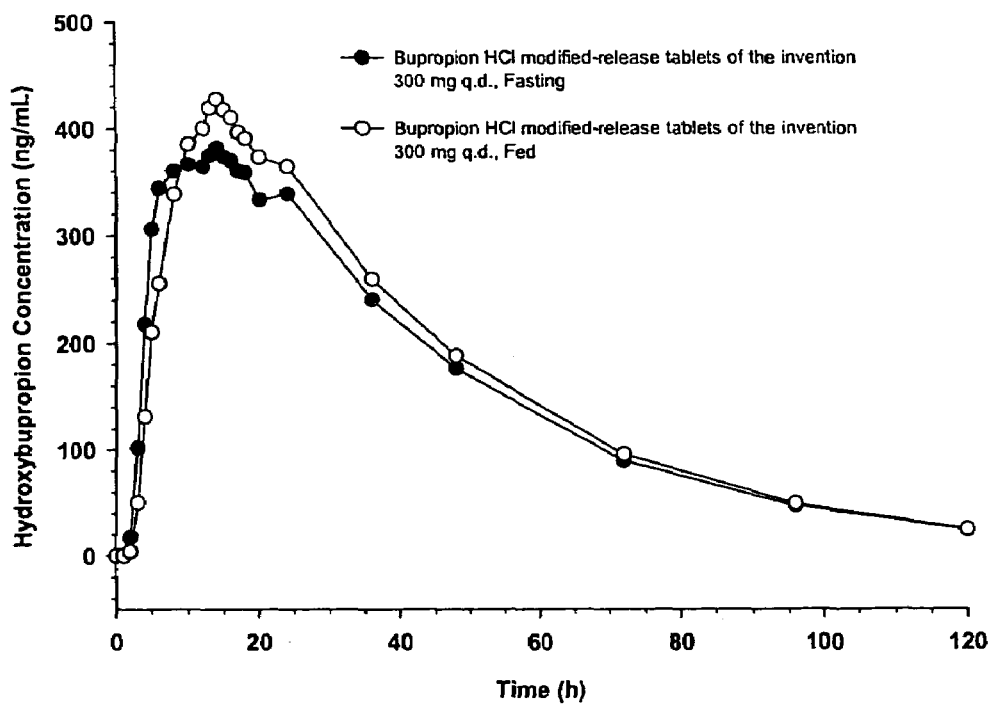
FIG. 5B is a graph comparing the effect of food on the mean plasma hydroxybupropion concentrations of a single dose once-daily 300 mg dosage strength modified-release bupropion hydrochloride tablet according to an embodiment of the invention.
Figure 5C:
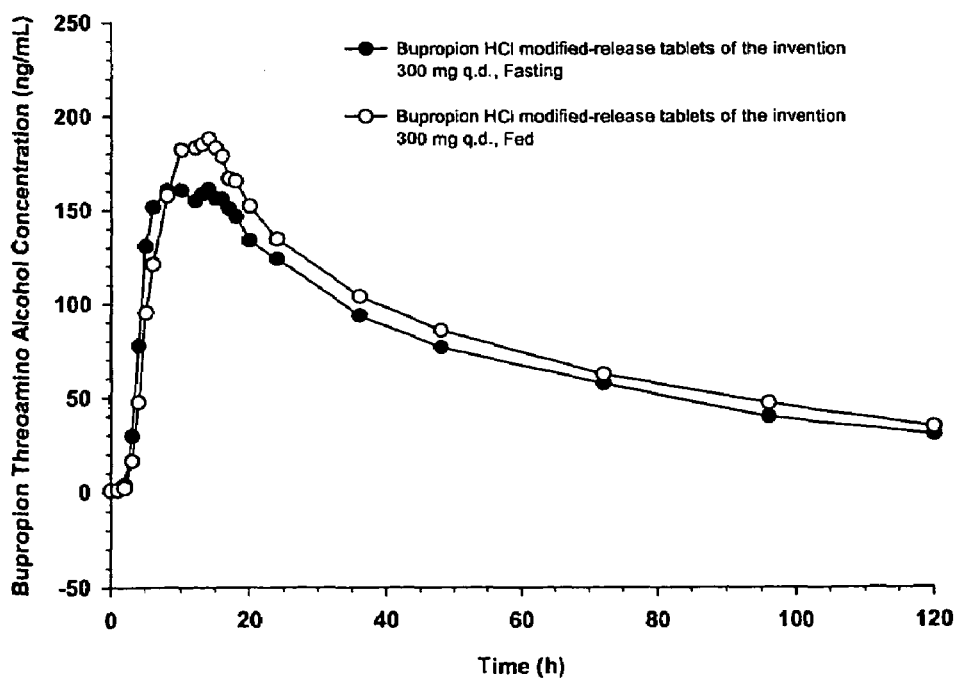
FIG. 5C is a graph comparing the effect of food on the mean plasma bupropion threoamino alcohol concentrations of a single dose once-daily 300 mg dosage strength modified-release bupropion hydrochloride tablet according to an embodiment of the invention.
Figure 5D:
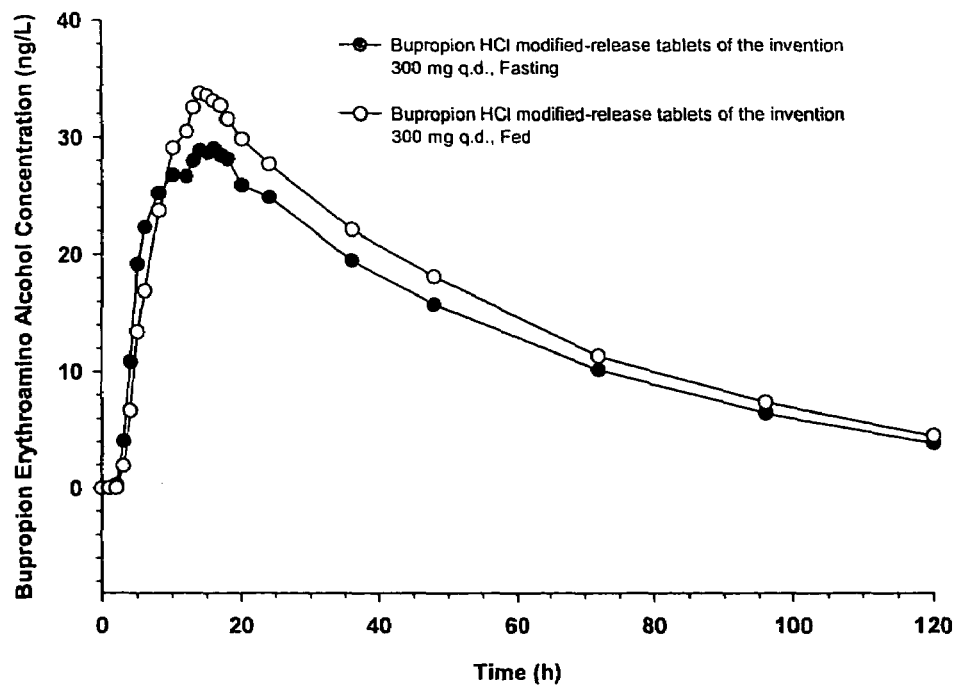
FIG. 5D is a graph comparing the effect of food on the mean plasma bupropion threoamino alcohol concentrations of a single dose once-daily 300 mg dosage strength modified-release bupropion hydrochloride tablet according to an embodiment of the invention.
Figure 6A:
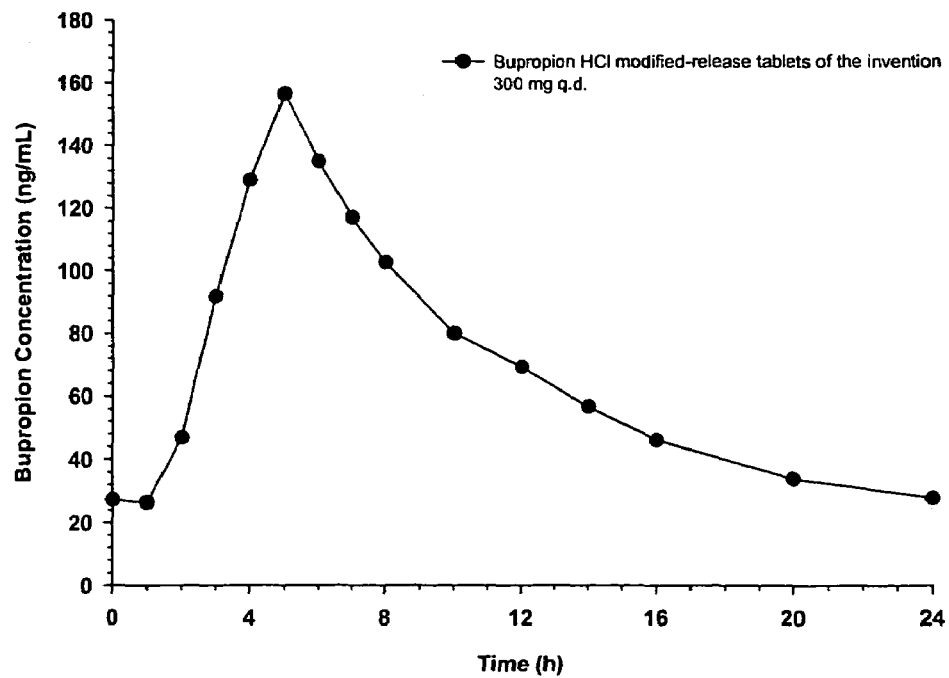
FIG. 6A is a graph illustrating the mean steady state blood plasma bupropion concentrations after multiple dosing of a once daily 300 mg modified-release bupropion hydrochloride tablet according to an embodiment of the invention when administered to a patient in the fasted state.
Figure 6B:
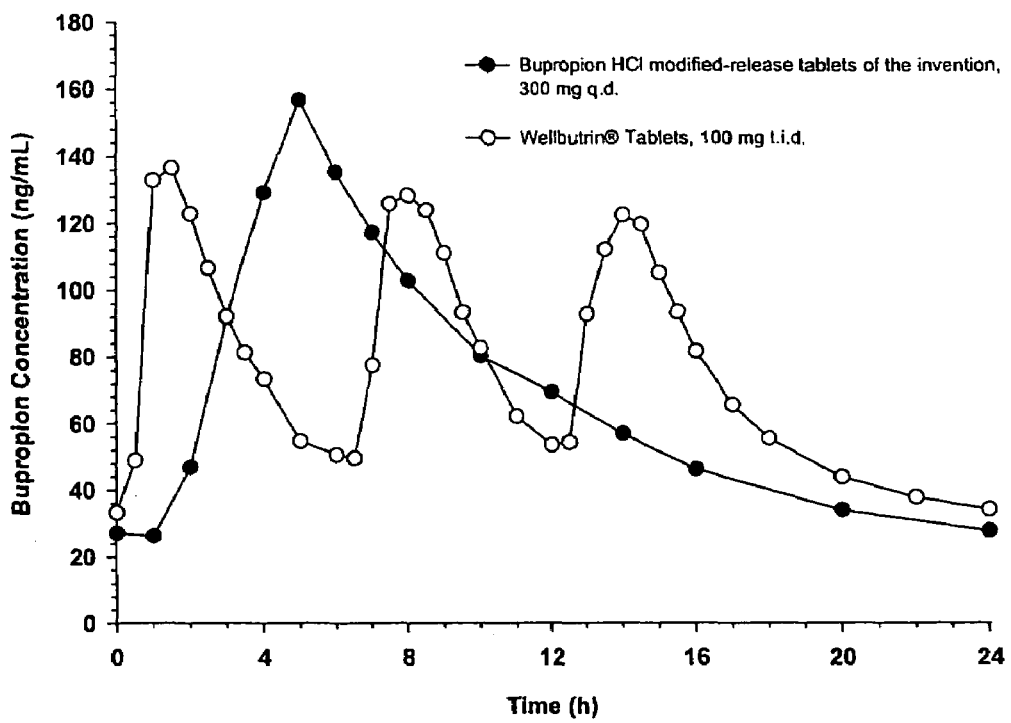
FIG. 6B is a graph comparing the mean steady state blood plasma bupropion concentrations shown in FIG. 5A with the mean steady state plasma bupropion concentrations after multiple dosing of the prior art Wellbutrin® tablet in the fasted state.
Figure 6C:
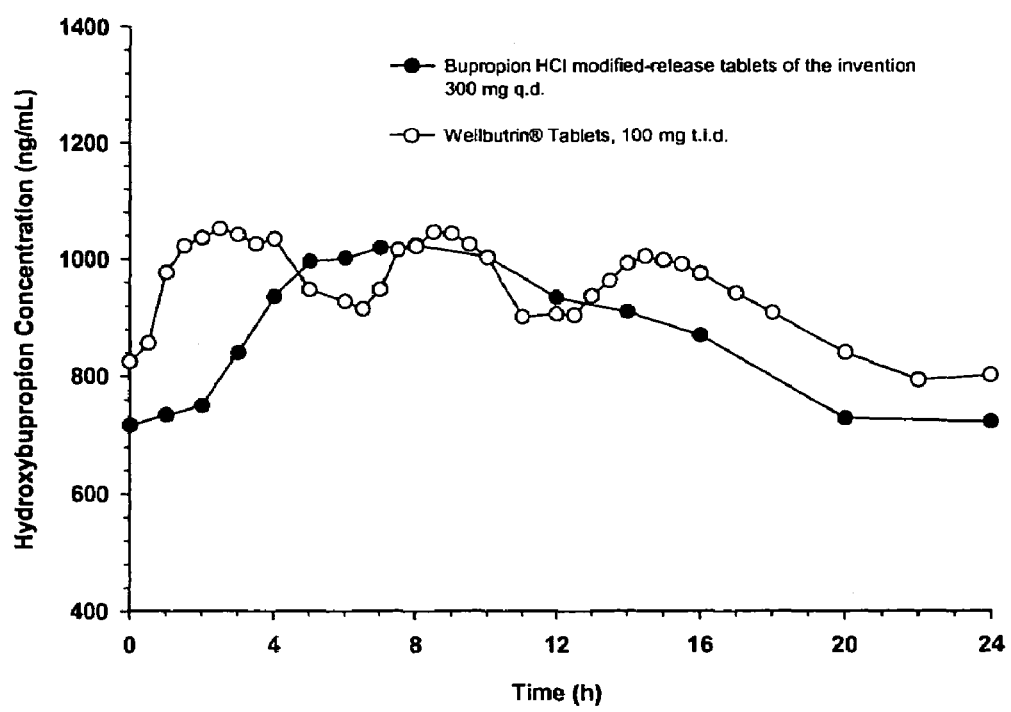
FIG. 6C is a graph comparing the mean steady state blood plasma hydroxybupropion concentrations after multiple dosing of a once daily 300 mg modified-release bupropion hydrochloride tablet according to an embodiment of the invention when administered to a patient in the fasted state with the mean steady state plasma hydroxybupropion concentrations after multiple dosing of the prior art Wellbutrin® tablet in the fasted state.
Figure 6D:
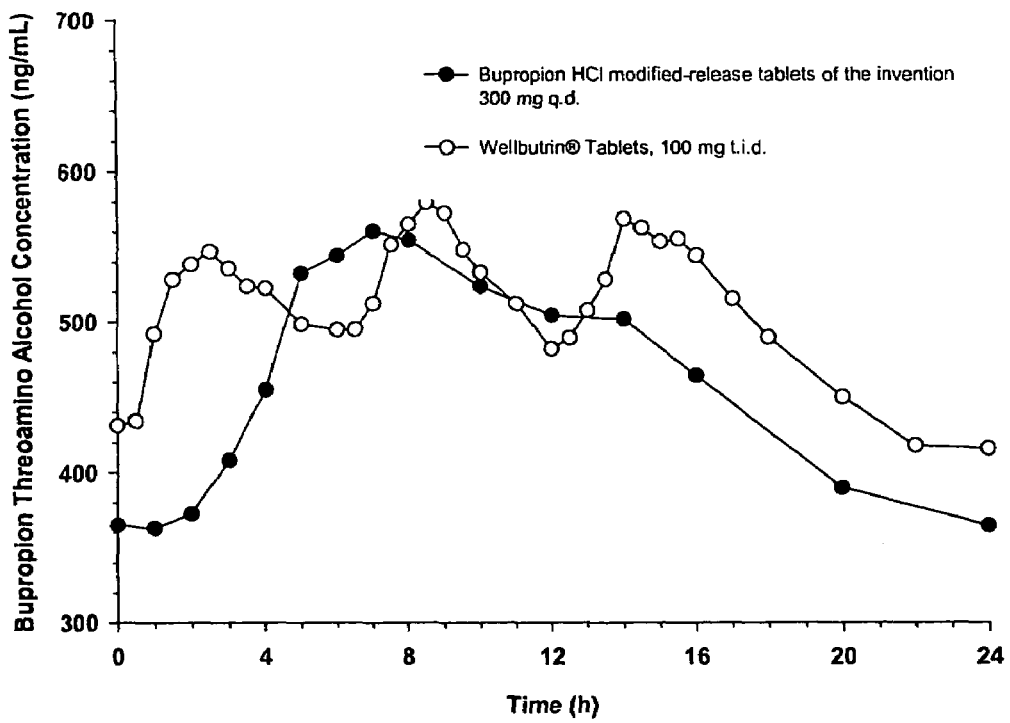
FIG. 6D is a graph comparing the mean steady state blood plasma bupropion threoamino alcohol concentrations after multiple dosing of a once daily 300 mg modified-release bupropion hydrochloride tablet according to an embodiment of the invention when administered to a patient in the fasted state with the mean steady state plasma bupropion threoamino alcohol concentrations after multiple dosing of the prior art Wellbutrin® tablet in the fasted state.
Figure 6E:
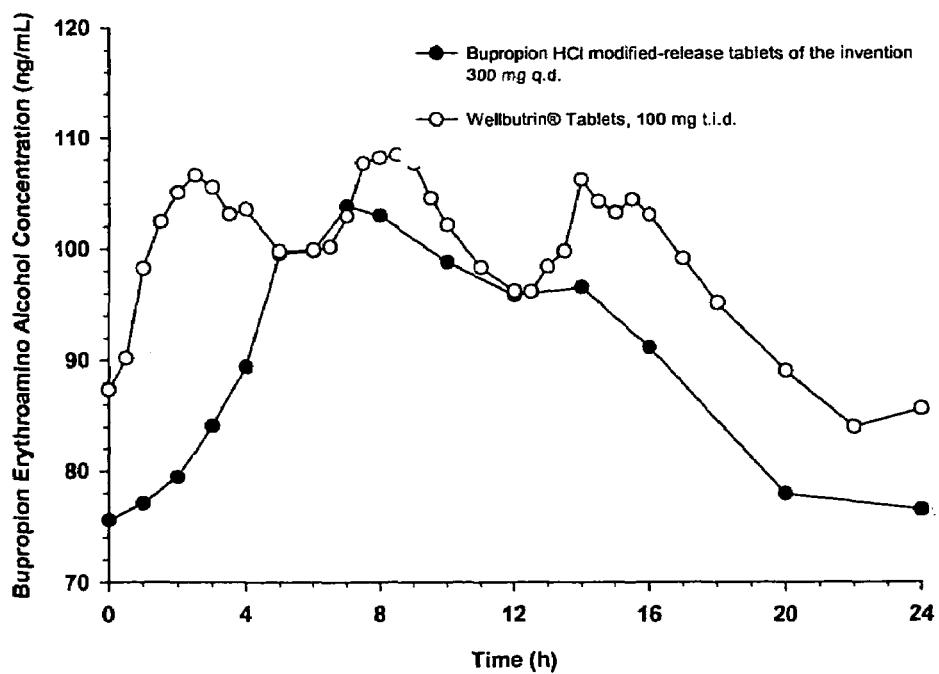
FIG. 6E is a graph comparing the mean steady state blood plasma bupropion erythroamino alcohol concentrations after multiple dosing of a once daily 300 mg modified-release bupropion hydrochloride tablet according to an embodiment of the invention when administered to a patient in the fasted state with the mean steady state plasma bupropion erythroamino alcohol concentrations after multiple dosing of the prior art Wellbutrin® tablet in the fasted state.
Figure 7A:
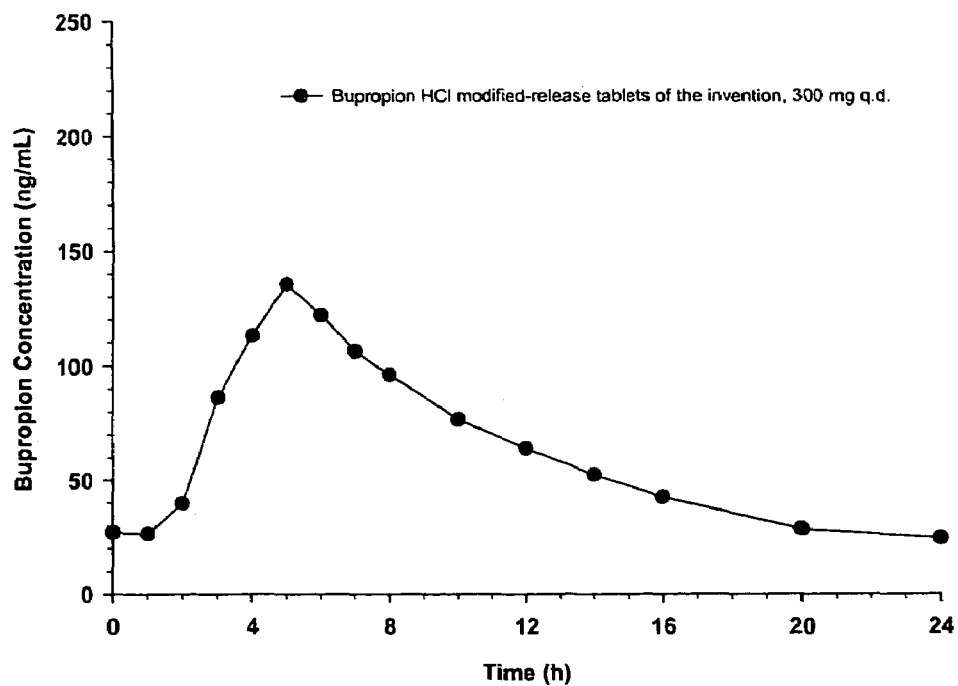
FIG. 7A is a graph illustrating the mean steady state blood plasma bupropion concentrations after multiple dosing of a once daily 300 mg modified-release bupropion hydrochloride tablet according to an embodiment of the invention under fasted conditions.
Figure 7B:
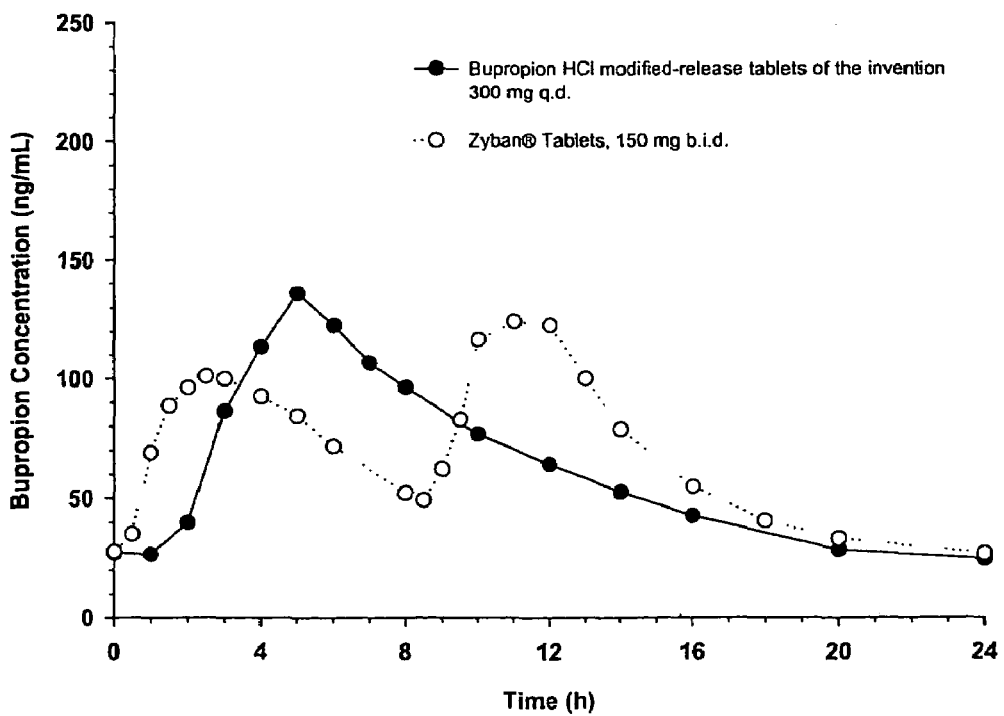
FIG. 7B is a graph comparing the mean steady state blood plasma bupropion concentrations shown in FIG. 7A with the mean steady state blood plasma bupropion concentrations after multiple dosing of the prior art 150 mg (b.i.d.) Zyban® tablets under fasted conditions.
Figure 7C:
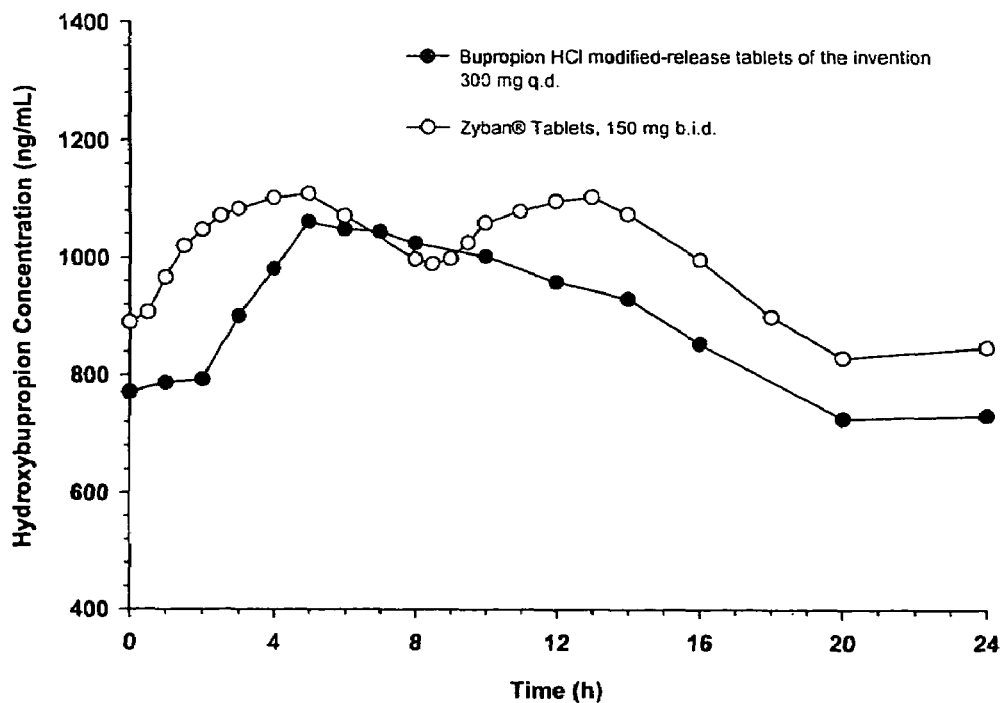
FIG. 7C is a graph comparing the mean steady state blood plasma hydroxybupropion concentrations after multiple dosing of a once daily 300 mg modified-release bupropion hydrochloride tablet according to an embodiment of the invention under fasted conditions with the mean steady state blood plasma hydroxybupropion concentrations after multiple dosing of the prior art 150 mg (b.i.d.) Zyban® tablets under fasted conditions.
Figure 7D:
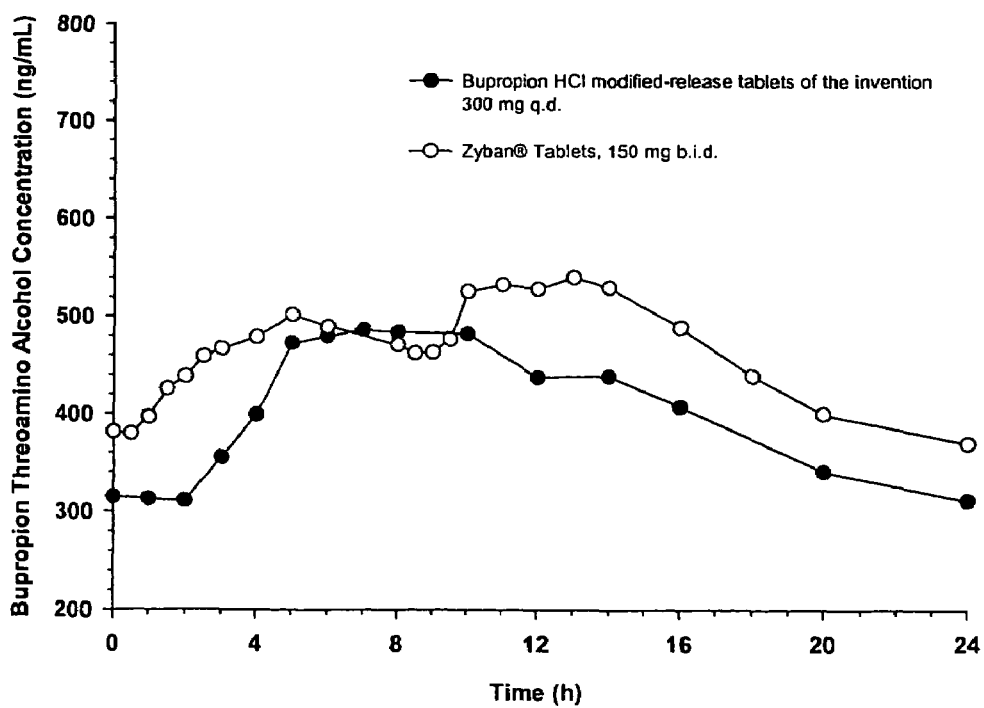
FIG. 7D is a graph comparing the mean steady state blood plasma bupropion threoamino alcohol concentrations after multiple dosing of a once daily 300 mg modified-release bupropion hydrochloride tablet according to an embodiment of the invention under fasted conditions with the mean steady state blood plasma bupropion threoamino alcohol concentrations after multiple dosing of the prior art 150 mg (b.i.d.) Zyban® tablets under fasted conditions.
Figure 7E:
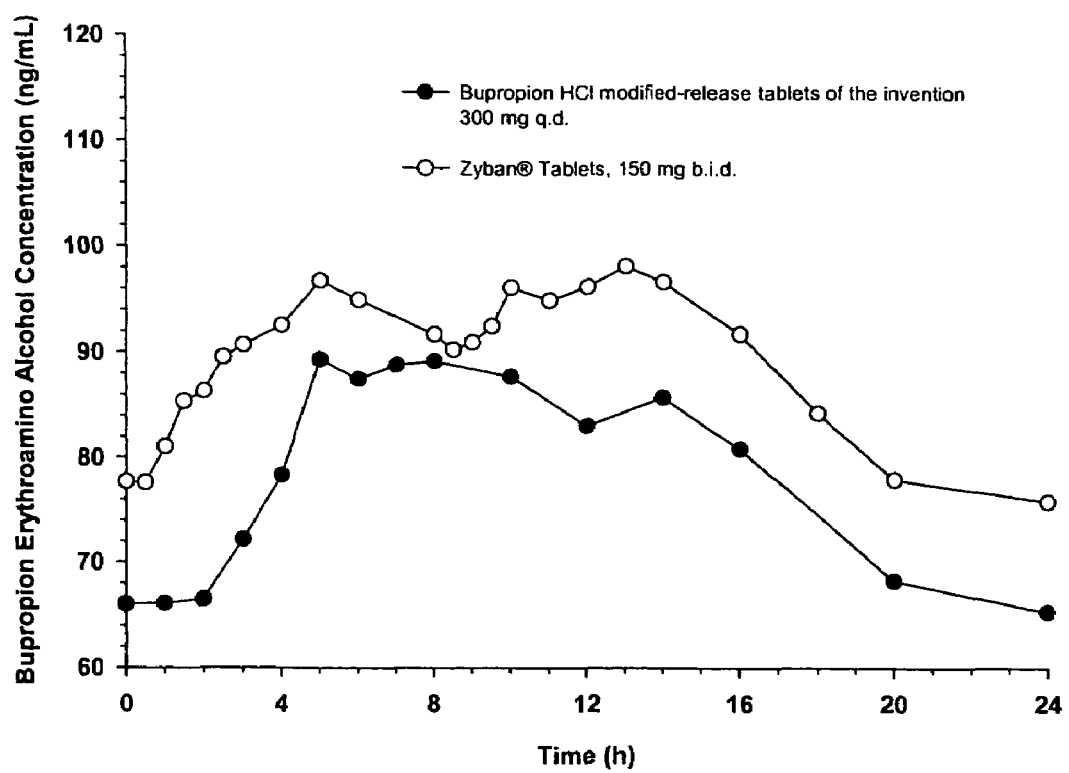
FIG. 7E is a graph comparing the mean steady state blood plasma bupropion erythroamino alcohol concentrations after multiple dosing of a once daily 300 mg modified-release bupropion hydrochloride tablet according to an embodiment of the invention under fasted conditions with the mean steady state blood plasma bupropion erythroamino alcohol concentrations after multiple dosing of the prior art 150 mg (b.i.d.) Zyban® tablets under fasted conditions.

The stability data to 48 months were evaluated by statistical expiry analysis for each modified-release tablet dosage strength. Expiry plots are presented in FIGS. 2A and 2B. The "data driven" specifications were derived by assessing the level of the upper confidence interval projected to 48 months.

EXAMPLE 2

1. The Moisture Barrier is not an Enteric Coat

The purpose of this study was to show that the modified release bupropion hydrochloride tablets of the invention are not enteric coated. The modified release formulation is based on a tablet core comprising bupropion hydrochloride, a binder and a lubricant. The tablet core is coated with a control-releasing coat, which functions to control the release of the bupropion hydrochloride. The control-releasing coated tablet cores are subsequently coated with a moisture barrier, which substantially impedse or retards absorption of moisture.

The release of the drug was measured spectrophotometrically by a two-stage dissolution procedure using USP enteric coating dissolution conditions method B (Basket at 75 rpm) to evaluate the tablet integrity. The results of the tests are shown in Tables 11 and 12:

TABLE 11

| Time | Acid Stage: % dissolved of 300 mg modified release bupropion HCl tablets | | | | | | | |
|---|---|---|---|---|---|---|---|---|
| (hr) | V1 | V2 | V3 | V4 | V5 | V6 | Mean | SD |
| 0 | 0.0 | 0.0 | 0.0 | 0.0 | 0.0 | 0.0 | 0.0 | 0.0 |
| 1 | 0.1 | 0.0 | 0.6 | 0.5 | 1.2 | 0.2 | 0.3 | 0.7 |
| 2 | 3.1 | 1.7 | 9.7 | 7.3 | 10.2 | 7.2 | 6.5 | 3.5 |

TABLE 12

| Time | Buffer Stage: % dissolved of 300 mg modified release bupropion HCl tablets | | | | | | | |
|---|---|---|---|---|---|---|---|---|
| (hr) | V1 | V2 | V3 | V4 | V5 | V6 | Mean | SD |
| 1 | 21.8 | 20.3 | 19.2 | 21.2 | 21.6 | 20.3 | 20.7 | 1.0 |
| 2 | 35.2 | 34.6 | 32.4 | 34.9 | 33.9 | 32.9 | 34.0 | 1.1 |
| 3 | 45.0 | 45.1 | 43.3 | 45.5 | 42.8 | 43.5 | 44.2 | 1.2 |
| 4 | 53.2 | 55.0 | 51.1 | 53.1 | 50.6 | 51.2 | 52.3 | 1.7 |
| 5 | 59.6 | 64.6 | 57.2 | 59.5 | 58.0 | 57.4 | 59.4 | 2.8 |
| 6 | 64.7 | 70.7 | 62.2 | 65.1 | 66.7 | 62.7 | 65.3 | 3.1 |
| 7 | 69.1 | 75.1 | 66.6 | 69.4 | 71.7 | 67.1 | 69.8 | 3.2 |
| 8 | 74.4 | 78.1 | 70.1 | 73.0 | 75.8 | 71.8 | 73.9 | 2.9 |
| 9 | 78.8 | 80.1 | 73.2 | 75.8 | 77.6 | 75.7 | 76.9 | 2.5 |
| 10 | 81.6 | 81.5 | 75.5 | 77.7 | 78.6 | 77.8 | 78.8 | 2.4 |
| 11 | 83.2 | 82.5 | 77.2 | 79.3 | 79.5 | 79.1 | 80.1 | 2.3 |
| 12 | 84.1 | 83.1 | 78.0 | 80.6 | 80.0 | 79.9 | 81.0 | 2.3 |
| 13 | 84.6 | 83.7 | 78.4 | 81.3 | 80.2 | 80.4 | 81.4 | 2.3 |
| 14 | 84.9 | 84.0 | 78.6 | 81.5 | 80.2 | 80.8 | 81.7 | 2.4 |

At acidic pH (0.1N HCl), about 7% of the bupropion hydrochloride is released within 2 hours, however at pH 6.8 about 21% of the bupropion hydrochloride is released within 1 hour. Accordingly, the modified release tablet of the invention does not meet the USP requirement of an enteric-coated tablet i.e., after 2 hours in acidic media (0.1N HCl) no individual values exceed 10% dissolved active drug and not less than 75% dissolved at 45 minutes in pH 6.8 buffer.

The functionality of the moisture barrier as a non-enteric coat was further shown by directly coating 150 mg tablet cores with the moisture barrier. Table 13 shows that the dissolution results (the first 2 hours in acidic medium) do not comply with the USP requirements for an enteric-coated tablet.

Medium: 900 ml 0.1 N HCl
Method: USP Apparatus type I at 75 rpm at 37° C.

TABLE 13

| Time | % Bupropion Hydrochloride dissolved | | | | | | | | |
|---|---|---|---|---|---|---|---|---|---|
| (hr) | V1 | V2 | V3 | V4 | V5 | V6 | Mean | SD | % RSD |
| 0 | 0.0 | 0.0 | 0.0 | 0.0 | 0.0 | 0.0 | 0.0 | 0.0 | 0.0 |
| 1 | 45.6 | 41.7 | 39.8 | 46.5 | 42.4 | 50.1 | 44.3 | 3.8 | 8.5 |
| 2 | 75.5 | 73.7 | 69.1 | 76.4 | 71.3 | 84.6 | 75.1 | 5.4 | 7.2 |
| 3 | 93.9 | 98.4 | 95.1 | 93.4 | 89.4 | 100.9 | 95.2 | 4.0 | 4.2 |
| 4 | 99.1 | 99.1 | 102.2 | 102.0 | 99.0 | 102.5 | 100.6 | 1.7 | 1.7 |
| 5 | 99.5 | 99.1 | 102.2 | 103.5 | 101.7 | 102.5 | 101.4 | 1.8 | 1.7 |

A buffer test was not performed due to the high release in the acidic medium.

2. The Moisture Barrier Functions to Substantially Impede or Retard the Absorption of Moisture.

The functionality of the moisture barrier as a coat which substantially impedes or retards the absorption of moisture was confirmed by determining the Karl-Fischer moisture content of either control-releasing coated tablet cores or moisture barrier coated tablet cores for the 300 mg tablet cores. The preparation for the formulations is as described in Example 1. The respective coated tablets were placed separately under accelerated conditions (40° C.±2° C./75% RH±5% RH) in an open glass dish for 10 days. As shown in Table 14, the moisture content for the control-releasing coated tablet cores are higher than for the moisture barrier coated tablet cores.

TABLE 14

| | % KF Moisture Content |
|---|---|
| Control-releasing Coated Tablet Cores | 0.7 |
| Moisture barrier Coated Tablet Cores | 0.45 |

The data presented in Tables 13 and 14 demonstrate that the moisture barrier does not function as an enteric coat as defined by the USP. Instead, the data demonstrate the functionality of the moisture barrier as a coat, which substantially impedes or retards the absorption of moisture.

EXAMPLE 3

The objective of this study was to investigate the dosage strength equivalency of the following test 150 mg and 300 mg product strengths of Bupropion HCl modified-release tablets under fasting conditions. A two-way, crossover, open-label, single-dose, fasting, dosage strength equivalency study of two strengths (150 mg and 300 mg) of bupropion HCl modified-release tablets of the invention was conducted. The modified-release tablets of the invention were administered once daily in normal healthy non-smoking male and female subjects.

The study design involved a 2-period, 2-treatment, single-dose crossover design under fasting conditions. The study periods were separated by a 3-week washout period. A total of 36 subjects (19 Male, 17 Female) enrolled for the study of which 35 of the subjects (19 Male, 16 Female) completed the study. Subjects were administered the following treatments:

A) 2×150 mg q.d. modified-release bupropion hydrochloride tablets of the invention administered orally with 240 mL of ambient temperature water following an overnight fast of at least 10 hours.

B) 1×300 mg q.d. modified-release bupropion hydrochloride tablets of the invention administered orally with 240 mL of ambient temperature water following an overnight fast of at least 10 hours.

The graphical mean plasma-concentration (ng/ml) profiles of bupropion and its metabolites hydroxybupropion, bupropion threoamino alcohol, and erythroamino alcohol over a 120-hour time period after administration of the 2×150 mg once daily and the 1×300 mg once daily dosage forms are shown in FIGS. 3A-D respectively.

Tables 15a-d provide the mean (±SD) pharmacokinetic data for bupropion following administration of the 2×150 mg dosage strength tablet administered once daily or the 300 mg dosage strength tablet administered once daily:

TABLE 15a (Bupropion)

| Pharmacokinetic Parameter (mean ± SD) | Bupropion HCl 2 × 150 mg Modified Release Tablets of the Invention (n = 35) | Bupropion HCl 1 × 300 mg Modified-Release Tablets of the Invention (n = 35) |
|---|---|---|
| $AUC_{0-t}$ (ng · hr/mL) | 1648.85 ± 475.34 | 1676.61 ± 474.09 |
| $AUC_{0-inf}$ (ng · hr/mL) | 1702.69 ± 489.30 | 1728.34 ± 478.43 |
| $C_{max}$ (ng/mL) | 150.11 ± 37.22 | 146.88 ± 47.61 |
| $T_{max}$ (hours) | 4.99 ± 0.76 | 5.20 ± 0.88 |
| $T_{1/2}$ (hours) | 22.70 ± 7.42 | 21.84 ± 7.35 |
| $K_{el}$ (hour$^{-1}$) | 0.036 ± 0.017 | 0.037 ± 0.018 |
| MRT (hours) | 22.28 ± 5.50 | 22.92 ± 5.50 |

TABLE 15b (Hydroxybupropion)

| Pharmacokinetic Parameter (mean ± SD) | Bupropion HCl 2 × 150 mg Modified Release Tablets of the Invention (n = 35) | Bupropion HCl × 300 mg Modified Release Tablets of the Invention (n = 35) |
|---|---|---|
| $AUC_{0-t}$ (ng · hr/mL) | 22506.34 ± 9372.50 | 22380.32 ± 8740.47 |
| $AUC_{0-inf}$ (ng · hr/mL) | 23634.19 ± 10373.91 | 23498.81 ± 9584.58 |
| $C_{max}$ (ng/mL) | 492.97 ± 182.28 | 479.23 ± 172.64 |
| $T_{max}$ (hours) | 11.66 ± 5.64 | 14.06 ± 5.10 |
| $t_{1/2}$ (hours) | 24.01 ± 4.85 | 24.09 ± 4.57 |
| $K_{el}$ (hour$^{-1}$) | 0.030 ± 0.007 | 0.030 ± 0.006 |
| MRT (hours) | 39.93 ± 6.94 | 41.18 ± 7.07 |
| M/P ratio | 13.4886 ± 5.3391 | 13.2966 ± 5.0489 |

TABLE 15c (Bupropion Threoamino Alcohol)

| Pharmacokinetic Parameter (mean ± SD) | Bupropion HCl 2 × 150 mg Modified Release Tablets of the Invention (n = 35) | Bupropion HCl 1 × 300 mg Modified Release Tablets of the Invention (n = 35) |
|---|---|---|
| $AUC_{0-t}$ (ng · hr/mL) | 7548.05 ± 3627.79 | 7262.88 ± 3083.24 |
| $AUC_{0-inf}$ (ng · hr/mL) | 9428.73 ± 4982.30 | 9091.33 ± 3926.24 |
| $C_{max}$ (ng/mL) | 173.22 ± 60.80 | 162.24 ± 58.97 |
| $T_{max}$ (hours) | 7.76 ± 2.65 | 8.47 ± 3.41 |
| $t_{1/2}$ (hours) | 50.47 ± 16.76 | 51.51 ± 16.83 |
| $K_{el}$ (hour$^{-1}$) | 0.015 ± 0.005 | 0.015 ± 0.005 |
| MRT (hours) | 69.31 ± 22.44 | 71.33 ± 21.93 |
| M/P ratio | 5.4378 ± 2.1088 | 5.2774 ± 2.0478 |

TABLE 15d (Bupropion Erythroamino Alcohol)

| Pharmacokinetic Parameter (mean ± SD) | Bupropion HCl 2 × 150 mg Extended Release Tablets of the Invention (n = 35) | Bupropion HCl 1 × 300 mg Extended Release Tablets of the Invention (n = 35) |
|---|---|---|
| $AUC_{0-t}$ (ng · hr/mL) | 1508.79 ± 601.87 | 1441.85 ± 495.53 |
| $AUC_{0-inf}$ (ng · hr/mL) | 1702.71 ± 777.29 | 1613.65 ± 623.69 |
| $C_{max}$ (ng/mL) | 28.88 ± 6.54 | 27.52 ± 6.67 |
| $T_{max}$ (hours) | 13.03 ± 3.48 | 15.24 ± 4.15 |
| $t_{1/2}$ (hours) | 32.15 ± 8.65 | 32.12 ± 9.22 |
| $K_{el}$ (hour$^{-1}$) | 0.023 ± 0.007 | 0.023 ± 0.006 |
| MRT (hours) | 51.60 ± 12.65 | 52.34 ± 13.44 |
| M/P ratio | 0.9985 ± 0.3678 | 0.9527 ± 0.3863 |

The relative (2×150 mg (q.d.) vs. 1×300 mg (q.d.)) bioavailability analysis results for $AUC_{0-inf}$, $AUC_{0-t}$, and $C_{max}$, transformed using the natural logarithm under fasting conditions is summarized in Table 16 for bupropion and its metabolites:

TABLE 16

| Parameter | 90% C.I. | Ratio of Geometric Means | Intra-Subject CV | 90% C.I. | Ratio of Geometric Means | Intra-Subject CV |
|---|---|---|---|---|---|---|
| | Bupropion | | | Hydroxybupropion | | |
| $AUC_{0-t}$ | 93.96%-102.76% | 98.26% | 11.07% | 94.42%-106.07% | 100.08% | 14.37% |
| $AUC_{0-inf}$ | 93.97%-102.88% | 98.32% | 11.19% | 94.23%-105.81% | 99.85% | 14.32% |
| $C_{max}$ | 97.77%-110.30% | 103.84% | 14.90% | 97.76%-108.17% | 102.84% | 12.51% |
| | Bupropion Threoamino Alcohol | | | Bupropion Erythroamino Alcohol | | |
| $AUC_{0-t}$ | 96.66%-109.16% | 102.72% | 15.03% | 96.83%-110.30% | 103.34% | 16.09% |
| $AUC_{0-inf}$ | 94.87%-108.57% | 101.49% | 16.66% | 97.09%-110.89% | 103.76% | 16.42% |
| $C_{max}$ | 100.06%-114.03% | 106.82% | 16.16% | 99.41%-111.26% | 105.17% | 13.91% |

The data shows that both the 150 mg dosage strength tablet given as two tablets once daily and 300 dosage strength tablet given once daily of the modified-release tablets of the invention as described herein and in Example 1 are equivalent to each other in terms of their pharmacokinetic parameters for bupropion and its metabolites.

EXAMPLE 4

A four-way, crossover, open-label, single-dose, fasting and food-effect comparative bioavailability study of bupropion hydrochloride modified-release 150 mg tablets as described herein and in Example 1 and Zyban® 150 mg tablets in normal healthy non-smoking male and female subjects were conducted. This study was designed to evaluate the rate and extent of absorption of bupropion in the fed and fasted state after administration of 150 mg dosage strength bupropion hydrochloride modified-release tablets as described herein and in Example 1. In parallel, the rate and extent of absorption of bupropion in the fed and fasted state after administration of 150 mg dosage strength Zyban® tablets was also evaluated in this study.

The study design followed a 2-period, 2-treatment, single-dose crossover design under fasting and fed conditions. The study periods were separated by a 2-week washout period. A total of 35 subjects (24 Male, 11 Female) were enrolled in the study of which 32 of the subjects (22 Male, 10 Female) completed the study. Subjects were administered the following treatments:

A) 150 mg q.d. modified-release bupropion hydrochloride tablets of the invention under fasting conditions,
B) 150 mg q.d. modified-release bupropion hydrochloride tablets of the invention under fed conditions,
C) 150 mg q.d. Zyban® tablets under fasting conditions, and
D) 150 mg q.d. Zyban® tablets under fed conditions.

The graphical mean plasma-concentration (ng/ml) profiles of bupropion and its metabolites hydroxybupropion, bupropion threoamino alcohol, and erythroamino alcohol over a 72-hour time period after administration of the 1×150 mg once daily modified-release tablets of the invention and the 1×150 mg once daily dosage form of Zyban® are shown in FIGS. 4A-E.

Table 17 provides the mean (±SD) pharmacokinetic data for bupropion following administration of the 150 mg dosage strength modified-release tablets of the invention or the commercially available prior art Zyban® tablets under fasting and fed conditions for bupropion and its metabolites:

TABLE 17

| | Geometric Mean Arithmetic Mean ± SD (% CV) | | | |
| --- | --- | --- | --- | --- |
| Pharmacokinetic Parameter | Bupropion HCl 150 mg Modified Release Tablets (Fasted) (n = 32) | Bupropion HCl 150 mg Modified Release Tablets of the Invention (Fed) (n = 32) | Zyban ® 150 mg Tablets (Fasted) (n = 32) | Zyban ® 150 mg Tablets (Fed) (n = 32) |
| Bupropion | | | | |
| $AUC_{0-t}$ (ng · hr/mL) | 825.1787 <br> 864.56 ± 259.86 <br> (30.06) | 882.1834 <br> 918.59 ± 271.21 <br> (29.52) | 840.5866 <br> 881.48 ± 270.64 <br> (30.70) | 1002.9491 <br> 1048.50 ± 306.63 <br> (29.24) |
| $AUC_{0-inf}$ (ng · hr/mL) | 886.1622* <br> 923.43 ± 263.01 <br> (28.48) | 926.4870* <br> 966.18 ± 290.02 <br> (30.02) | 884.2148* <br> 929.01 ± 291.01 <br> (31.32) | 1043.8802* <br> 1092.41 ± 326.05 <br> (29.85) |
| $C_{max}$ (ng/mL) | 78.2884 <br> 81.78 ± 24.47 <br> (29.93) | 73.1637 <br> 75.75 ± 19.77 <br> (26.10) | 92.1115 <br> 96.96 ± 31.38 <br> (32.37) | 124.3873 <br> 128.81 ± 32.03 <br> (24.87) |
| $T_{max}$ (hours)† | 5.13 ± 1.13 <br> (22.02) | 6.59 ± 2.18 <br> (33.10) | 3.04 ± 0.77 <br> (25.41) | 3.88 ± 1.01 <br> (25.99) |
| $t_{1/2}$ (hours)† | 18.17 ± 6.35* <br> (34.97) | 19.26 ± 6.77* <br> (35.15) | 19.88 ± 5.91* <br> (29.75) | 19.48 ± 5.45* <br> (27.99) |
| $K_{el}$ (hour$^{-1}$)† | 0.044 ± 0.018* <br> (41.996) | 0.041 ± 0.017* <br> (42.214) | 0.039 ± 0.017* <br> (42.096) | 0.039 ± 0.015* <br> (38.386) |
| $MRT_{0-inf}$ (hours)† | 4.81 ± 2.38* <br> (49.43) | 5.18 ± 2.99* <br> (57.81) | 4.69 ± 2.25* <br> (47.93) | 4.34 ± 2.00* <br> (46.08) |
| Hydrobupropion | | | | |
| $AUC_{0-t}$ (ng · hr/mL) | 10745.045 <br> 12611.91 ± 8151.69 <br> (64.63) | 10939.113 <br> 12604.70 ± 7739.11 <br> (61.40) | 11514.933 <br> 12976.49 ± 6817.46 <br> (52.54) | 12975.263 <br> 14679.97 ± 8184.51 <br> (55.75) |
| $AUC_{0-inf}$ (ng · hr/mL) | 11209.310 <br> 13034.17 ± 8207.41 <br> (62.97) | 11383.270 <br> 13049.55 ± 7933.08 <br> (60.79) | 11910.790 <br> 13344.28 ± 6863.47 <br> (51.43) | 13397.186* <br> 15129.56 ± 8370.60 <br> (55.33) |
| $C_{max}$ (ng/mL) | 222.2716 <br> 245.61 ± 119.94 <br> (48.83) | 230.4191 <br> 252.46 ± 112.93 <br> (44.73) | 294.8008 <br> 316.89 ± 125.90 <br> (39.73) | 301.9918 <br> 325.85 ± 131.69 <br> (40.42) |
| $T_{max}$ (hours)† | 15.22 ± 6.14 <br> (40.32) | 15.38 ± 4.35 <br> (28.31) | 6.04 ± 1.18 <br> (19.56) | 7.19 ± 2.91 <br> (40.49) |
| $t_{1/2}$ (hours)† | 25.19 ± 5.90 <br> (23.42) | 25.26 ± 5.98 <br> (23.67) | 25.37 ± 6.14 <br> (24.21) | 25.68 ± 5.70* <br> (22.18) |
| $K_{el}$ (hour$^{-1}$)† | 0.029 ± 0.007 <br> (25.285) | 0.029 ± 0.008 <br> (26.635) | 0.029 ± 0.008 <br> (27.142) | 0.028 ± 0.006* <br> (22.223) |

TABLE 17-continued

| | Geometric Mean Arithmetic Mean ± SD (% CV) | | | |
|---|---|---|---|---|
| Pharmacokinetic Parameter | Bupropion HCl 150 mg Modified Release Tablets (Fasted) (n = 32) | Bupropion HCl 150 mg Modified Release Tablets of the Invention (Fed) (n = 32) | Zyban ® 150 mg Tablets (Fasted) (n = 32) | Zyban ® 150 mg Tablets (Fed) (n = 32) |
| $MRT_{0-inf}$ (hours)† | 5.78 ± 4.17 (72.15) | 5.78 ± 3.20 (55.43) | 4.84 ± 2.22 (45.85) | 4.01 ± 1.87* (46.57) |
| M/P ratio† | 3.851 ± 1.097 | 4.029 ± 1.210 | 3.874 ± 1.214 | 4.556 ± 1.360 |
| | Bupropion Threoamino Alcohol | | | |
| $AUC_{0-t}$ (ng · hr/mL) | 4223.4179 4686.42 ± 2736.63 (58.39) | 4397.5375 4969.37 ± 3229.17 (64.98) | 4376.0423 4832.84 ± 2671.85 (55.29) | 5042.7155 5478.16 ± 2694.10 (49.18) |
| $AUC_{0-inf}$ (ng · hr/mL) | 4466.6770 5006.42 ± 3088.85 (61.70) | 4702.2669 5360.00 ± 3691.31 (68.87) | 4644.3189 5147.80 ± 2897.63 (56.29) | 5346.5138 5853.85 ± 3083.18* (52.67) |
| $C_{max}$ (ng/mL) | 81.8673 88.43 ± 37.68 (42.61) | 87.4966 93.97 ± 36.82 (39.18) | 107.2111 112.12 ± 34.64 (30.90) | 124.7860 130.65 ± 40.68 (31.13) |
| $T_{max}$ (hours)† | 10.03 ± 3.62 (36.12) | 11.94 ± 3.39 (28.39) | 5.76 ± 1.02 (17.65) | 5.38 ± 0.95 (17.66) |
| $t_{1/2}$ (hours)† | 49.27 ± 14.83 (30.10) | 50.94 ± 15.39 (30.22) | 51.44 ± 14.06 (27.34) | 52.82 ± 14.82* (28.05) |
| $K_{el}$ (hour$^{-1}$)† | 0.015 ± 0.005 (30.287) | 0.015 ± 0.005 (30.636) | 0.014 ± 0.004 (26.839) | 0.014 ± 0.004* (31.030) |
| $MRT_{0-inf}$ (hours)† | 15.81 ± 12.98 (82.07) | 17.89 ± 13.50 (75.49) | 16.52 ± 12.41 (75.11) | 18.23 ± 14.02* (76.92) |
| M/P ratio† | 3.851 ± 1.097 | 4.029 ± 1.210 | 3.874 ± 1.214 | 4.556 ± 1.360 |
| | Bupropion Erythroamino Alcohol | | | |
| $AUC_{0-t}$ (ng · hr/mL) | 615.3554 675.24 ± 321.49 (47.61) | 662.8840 722.75 ± 341.87 (47.30) | 666.6066 716.66 ± 300.64 (41.95) | 766.3201 823.24 ± 320.87 (38.98) |
| $AUC_{0-inf}$ (ng · hr/mL) | 711.3752 768.15 ± 333.66 (43.44) | 754.6092 816.35 ± 372.52 (45.63) | 750.7705 802.32 ± 315.77 (39.36) | 839.2428 893.65 ± 330.20* (36.95) |
| $C_{max}$ (ng/mL) | 13.6946 14.17 ± 3.85 (27.14) | 14.6158 15.04 ± 3.56 (23.69) | 17.2653 17.55 ± 3.23 (18.39) | 18.1560 18.50 ± 3.84 (20.76) |
| $T_{max}$ (hours)† | 15.57 ± 4.65 (29.90) | 14.88 ± 3.09 (20.74) | 6.85 ± 1.92 (28.04) | 7.88 ± 3.83 (48.57) |
| $t_{1/2}$ (hours)† | 29.14 ± 8.77 (30.09) | 30.39 ± 10.17 (33.47) | 29.69 ± 9.37 (31.57) | 31.38 ± 10.74* (34.23) |
| $K_{el}$ (hour$^{-1}$)† | 0.026 ± 0.007 (28.240) | 0.025 ± 0.008 (31.201) | 0.026 ± 0.009 (34.415) | 0.024 ± 0.007* (30.060) |
| $MRT_{0-inf}$ (hours)† | 17.10 ± 6.30 (36.87) | 16.94 ± 9.04 (53.39) | 15.10 ± 5.65 (37.44) | 15.09 ± 6.62* (43.89) |
| M/P ratio† | 3.851 ± 1.097 | 4.029 ± 1.210 | 3.874 ± 1.214 | 4.556 ± 1.360 |

*n = 31

†Expressed as Arithmetic Mean ± SD (% CV)

The relative (modified-release tablets of the invention fasting vs. fed) bioavailability analysis results for $AUC_{0-inf}$, $AUC_{0-t}$, and $C_{max}$ transformed using the natural logarithm under both fasting and fasting conditions is summarized in Table 18 for bupropion and its metabolites:

TABLE 18

| Parameter | 90% C.I. | Ratio of Means | Intra-Subject CV | 90% C.I. | Ratio of Means | Intra-Subject CV |
|---|---|---|---|---|---|---|
| | Bupropion | | | Hydroxybupropion | | |
| $AUC_{0-t}$ | 101.74%-112.23% | 106.852% | 11.786% | 95.30%-109.76% | 102.275% | 16.971% |
| $AUC_{0-inf}$ | 100.18%-109.60% | 104.788% | 10.533% | 95.48%-108.95% | 101.993% | 15.844% |
| $C_{max}$ | 86.58%-100.13% | 93.107% | 17.470% | 97.20%-111.36% | 104.043% | 16.336% |
| | Bupropion Threoamino Alcohol | | | Bupropion Erythroamino Alcohol | | |
| $AUC_{0-t}$ | 98.77%-109.74% | 104.108% | 12.646% | 101.02%-114.99% | 107.780% | 15.564% |
| $AUC_{0-inf}$ | 100.03%-110.79% | 105.274% | 12.269% | 100.49%-112.09% | 106.132% | 13.127% |
| $C_{max}$ | 100.41%-113.77% | 106.884% | 14.998% | 101.23%-112.49% | 106.712% | 12.662% |

The data in Table 18 show that the bioavailability of bupropion and its metabolites does not show a food effect i.e., the modified-release tablets of the invention containing bupropion hydrochloride are bioequivalent in the presence or absence of food as evidenced by the fact that the 90% CI of the ratio of the geometric means for the $AUC_{0-inf}$ (and the $AUC_{0-t}$ when appropriate) and $C_{max}$ in the fasting vs. fed state fall within the FDA suggested limits of 80-125%.

EXAMPLE 5

A two-way, crossover, open-label, single-dose, food-effect, comparative bioavailability study of the 300 mg dosage strength bupropion hydrochloride modified-release tablets of the invention in normal healthy non-smoking male and female subjects.

The study was designed to evaluate the effect of food on the rate and extent of absorption of the once-daily 300 mg dosage strength bupropion hydrochloride modified-release tablets of the invention under single-dose conditions. The study design followed a 2-period, 2-treatment, single-dose crossover design under fasting and fed conditions. The study periods were separated by a 2-week wash out period. A total of 36 subjects (26 Male, 10 Female) were enrolled in the study of which 32 of the subjects (23 Male, 9 Female) completed the study. Subjects were administered the following:

A) 1×300 mg modified-release tablet after a 1 hour fast.

B) 1×300 mg modified-release tablet after complete intake of a high fat breakfast.

The graphical mean plasma-concentration (ng/ml) profiles of bupropion and its metabolites hydroxybupropion, bupropion threoamino alcohol, and erythroamino alcohol over a 120-hour time period after administration of the 1×300 mg once daily modified-release tablets of the invention under fed and fasting conditions are shown in FIGS. 5A-D respectively.

Table 19 provides mean (±SD) pharmacokinetic data for bupropion and its metabolites following administration of the 300 mg dosage strength modified-release tablets of the invention under fasting and fed conditions:

TABLE 19

| Pharmacokinetic Parameter | Bupropion HCl 300 mg Modified Release Tablets (Fed) (n = 31) Mean ± SD | Bupropion HCl 300 mg Modified Release Tablets (Fasting) (n = 31) Mean ± SD |
|---|---|---|
| | Bupropion | |
| $AUC_{0-t}$ (ng · hr/mL) | 1775.45 ± 530.77 | 1628.38 ± 511.15 |
| $AUC_{0-inf}$ (ng · hr/mL) | 1832.54 ± 548.50 | 1678.36 ± 521.18 |
| $C_{max}$ (ng/mL) | 138.36 ± 42.35 | 151.35 ± 48.87 |
| $T_{max}$ (hour) | 6.16 ± 1.84 | 5.16 ± 0.86 |
| $t_{1/2}$ (hour) | 21.76 ± 5.85 | 21.21 ± 6.17 |
| $K_{el}$ (hour$^{-1}$) | 0.035 ± 0.011 | 0.036 ± 0.012 |
| MRT (hour) | 22.56 ± 4.60 | 21.58 ± 4.23 |
| | Hydroxybupropion | |
| $AUC_{0-t}$ (ng · hr/mL) | 19733.51 ± 9411.52 | 18938.84 ± 8387.21 |
| $AUC_{0-inf}$ (ng · hr/mL) | 20886.13 ± 10230.69 | 19852.73 ± 9049.54 |
| $C_{max}$ (ng/mL) | 449.05 ± 181.73 | 409.79 ± 154.84 |
| $T_{max}$ (hour) | 14.32 ± 3.18 | 13.71 ± 5.15 |
| $t_{1/2}$ (hour) | 24.11 ± 5.21 | 23.95 ± 4.84 |
| $K_{el}$ (hour$^{-1}$) | 0.030 ± 0.007 | 0.030 ± 0.007 |
| MRT (hour) | 42.03 ± 7.60 | 41.08 ± 6.13 |
| M/P Ratio | 10.5919 ± 3.8325 | 11.3178 ± 4.6281 |
| | Bupropion Threoamino Alcohol | |
| $AUC_{0-t}$ (ng · hr/mL) | 9769.69 ± 6136.11 | 9032.19 ± 6595.77 |
| $AUC_{0-inf}$ (ng · hr/mL) | 13280.57 ± 9398.23 | 11696.29 ± 9018.00 |
| $C_{max}$ (ng/mL) | 208.39 ± 98.15 | 182.52 ± 99.62 |
| $T_{max}$ (hour) | 12.26 ± 3.36 | 9.94 ± 4.84 |
| $t_{1/2}$ (hour) | 55.09 ± 17.66 | 55.25 ± 20.72 |
| $K_{el}$ (hour$^{-1}$) | 0.014 ± 0.004 | 0.014 ± 0.004 |
| MRT (hour) | 79.10 ± 25.10 | 78.60 ± 28.28 |
| M/P Ratio | 6.9435 ± 3.8129 | 6.6417 ± 3.4215 |
| | Bupropion Erythroamino Alcohol | |
| $AUC_{0-t}$ (ng · hr/mL) | 1803.45 ± 693.19 | 1634.56 ± 741.60 |
| $AUC_{0-inf}$ (ng · hr/mL) | 2116.01 ± 1026.23 | 1867.74 ± 971.96 |
| $C_{max}$ (ng/mL) | 35.80 ± 9.13 | 31.03 ± 9.97 |
| $T_{max}$ (hour) | 14.74 ± 2.71 | 14.16 ± 3.85 |

TABLE 19-continued

| Pharmacokinetic Parameter | Bupropion HCl 300 mg Modified Release Tablets (Fed) (n = 31) Mean ± SD | Bupropion HCl 300 mg Modified Release Tablets (Fasting) (n = 31) Mean ± SD |
|---|---|---|
| $t_{1/2}$ (hour) | 35.23 ± 12.03 | 33.89 ± 11.02 |
| $K_{el}$ (hour$^{-1}$) | 0.021 ± 0.006 | 0.022 ± 0.006 |
| MRT (hour) | 57.78 ± 17.49 | 54.75 ± 14.45 |
| M/P Ratio | 1.1322 ± 0.3876 | 1.0947 ± 0.3952 |

The relative (Fed vs. Fasting) bioavailability analysis results for $AUC_{0-inf}$, $AUC_{0-t}$, and $C_{max}$ transformed using the natural logarithm under both fasting and fasting conditions for bupriopion and its metabolites is summarized in Table 20:

TABLE 20

| Parameter | 90% C.I. | Ratio of Geometric Means | Intra-Subject CV | 90% C.I. | Ratio of Geometric Means | Intra-Subject CV |
|---|---|---|---|---|---|---|
| | Bupropion | | | Hydroxybupropion | | |
| $AUC_{0-t}$ | 104.00%-116.57% | 110.10% | 13.21% | 96.27%-111.84% | 103.76% | 17.36% |
| $AUC_{0-inf}$ | 104.18%-116.49% | 110.16% | 12.93% | 97.03%-112.72% | 104.58% | 17.35% |
| $C_{max}$ | 84.49%-100.86% | 92.31% | 20.50% | 103.44%-116.91% | 109.97% | 14.17% |
| | Bupropion Threoamino Alcohol | | | Bupropion Erythroamino Alcohol | | |
| $AUC_{0-t}$ | 104.31%-121.18% | 112.42% | 17.36% | 104.06%-123.56% | 113.39% | 19.89% |
| $AUC_{0-inf}$ | 104.15%-125.65% | 114.39% | 20.59% | 105.26%-126.61% | 115.44% | 21.39% |
| $C_{max}$ | 110.61%-124.96% | 117.57% | 14.12% | 110.14%-126.40% | 117.99% | 15.94% |

The data in Table 20 show that the bioavailability of bupropion and its metabolites from the 300 mg dosage strength modified-release bupropion hydrochloride tablets of the invention do not show a food effect as evidenced by the fact that the 90% CI of the ratio of the geometric means for the $AUC_{0-inf}$ (and the $AUC_{0-t}$ when appropriate) and $C_{max}$ in the fed vs. fasted state fall within the FDA suggested limits of 80-125%.

EXAMPLE 6

A two-way, crossover, steady state, multiple-dose, open-label, fasting, comparative bioavailability study of a once-daily bupropion hydrochloride 300 mg modified-release tablet of the invention versus the immediate release thrice daily Wellbutrin® 100 mg tablets in normal healthy non-smoking male and female subjects was conducted. This study was designed to evaluate the bioavailability of a once daily 300 mg dosage strength of the modified-release tablets of the invention relative to the commercially available prior art thrice daily immediate release Wellbutrin® tablets under steady-state, fasting conditions.

The study was designed as a 2-period, 2-treatment, dose escalated, multiple-dose crossover study under fasting conditions with a 2-week washout period between the two study periods. A total of 40 subjects (27 Males, 13 Females) were enrolled in the study of which 30 subjects (22 Males, 8 Females) completed the study. Subjects were administered the following dosing regimen:

A) Wellbutrin® 100 mg tablets were administered orally at 0.0 hours (starting at 7:00 AM) on Days 1, 2, and 3 (b.i.d.) with 240 ml of ambient temperature water following an overnight fast of at least 10 hours. All subjects also received a second dose of 1 Wellbutrin® 100 mg tablets at 12.0 hours with 240 ml of ambient temperature water after a fast of at least 1 hour. On days 4-13, subjects received one 300 mg dosage strength bupropion hydrochloride modified-release tablet of the invention at 0.0 hours (starting at 7: AM) with 240 ml of ambient temperature water following an overnight fast of at least 10 hours.

B) Wellbutrin® 100 mg tablets were administered orally at 0.0 hours (starting at 7:00 AM) on Days 1, 2, and 3 (b.i.d.) with 240 ml of ambient temperature water following an overnight fast of at least 10 hours. All subjects also received a second dose of 1 Wellbutrin® 100 mg tablet at 12.0 hours with 240 ml of ambient temperature water after a fast of at least 1 hour. On days 4-13, subjects received 1 Wellbutrin® 100 mg tablet at 0.0 hours (starting at 7:00 AM) with 240 ml of ambient temperature water, following an overnight fast of at least 10 hours. All subjects then received a second dose of 1 Wellbutrin® 100 mg tablet at 6.0 hours with 240 ml of ambient temperature water following a fast of at least 1 hour. All subjects also received a third dose of 1 Wellbutrin® 100 mg tablet at 12.0 hours with 240 ml of ambient temperature water, following a fast of at least 1 hour.

The graphical mean plasma-concentration (ng/ml) profiles of bupropion and its metabolites hydroxybupropion, bupropion threoamino alcohol, and erythroamino alcohol over the study period after administration of the 1×300 mg once daily modified-release tablets of the invention and the Wellbutrin® 3×100 mg tablets are shown in FIGS. 6A-E respectively.

Table 21 provides the mean (±SD) pharmacokinetic data for bupropion following administration of the once daily 300 mg dosage strength modified-release tablet of the invention or the thrice-daily commercially available prior art Wellbutrin® 100 mg tablet:

TABLE 21

| Pharmacokinetic Parameter | Bupropion HCl 300 mg Modified Release Tablets of the Invention (n = 30) (mean ± SD) | Wellbutrin ® 100 mg Tablets (n = 30) (mean ± SD) |
|---|---|---|
| | Bupropion | |
| $AUC_{0-\tau}$ (ng · hr/mL) | 1612.04 ± 490.27 | 1791.98 ± 483.43 |
| $C_{max}$ (ng/mL) | 167.50 ± 46.56 | 175.40 ± 56.03 |
| $C_{min}$ (ng/mL) | 27.64 ± 10.73 | 34.06 ± 12.49 |
| $T_{max}$ (hours) | 4.90 ± 0.89 | 1.60 ± 0.58 |
| Degree of Fluctuation (%) | 212.56 ± 39.42 | 189.98 ± 38.99 |
| $C_{ave}$ (ng/mL) | 67.17 ± 20.43 | 74.67 ± 20.14 |
| Degree of Swing (%) | 554.59 ± 193.21 | 439.58 ± 141.64 |
| M/P ratio | 12.92 ± 5.31 | 12.61 ± 5.11 |

TABLE 21-continued

| Pharmacokinetic Parameter | Bupropion HCl 300 mg Modified Release Tablets of the Invention (n = 30) (mean ± SD) | Wellbutrin ® 100 mg Tablets (n = 30) (mean ± SD) |
|---|---|---|
| Hydroxybupropion | | |
| $AUC_{0-\tau}$ (ng · hr/mL) | 20824.77 ± 7423.56 | 22456.08 ± 6889.20 |
| $C_{max}$ (ng/mL) | 1095.64 ± 385.06 | 1156.34 ± 339.34 |
| $C_{min}$ (ng/mL) | 722.23 ± 281.76 | 800.90 ± 262.97 |
| $T_{max}$ (hours) | 7.30 ± 2.45 | 2.47 ± 0.83 |
| Degree of Fluctuation (%) | 44.34 ± 16.57 | 40.78 ± 31.24 |
| $C_{ave}$ (ng/mL) | 867.70 ± 309.32 | 935.67 ± 287.05 |
| Degree of Swing (%) | 54.65 ± 22.48 | 49.19 ± 40.60 |
| M/P ratio | 7.01 ± 1.84 | 6.91 ± 1.81 |
| Bupropion Threoamino Alcohol | | |
| $AUC_{0-\tau}$ (ng · hr/mL) | 10987.88 ± 3193.09 | 12051.42 ± 3107.48 |
| $C_{max}$ (ng/mL) | 585.36 ± 155.83 | 629.81 ± 138.84 |
| $C_{min}$ (ng/mL) | 364.42 ± 122.60 | 415.71 ± 122.32 |
| $T_{max}$ (hours) | 7.83 ± 2.15 | 2.49 ± 0.81 |
| Degree of Fluctuation (%) | 50.47 ± 17.22 | 45.25 ± 21.80 |
| $C_{ave}$ (ng/mL) | 457.83 ± 133.05 | 502.14 ± 129.48 |
| Degree of Swing (%) | 65.68 ± 26.11 | 56.34 ± 29.48 |
| M/P ratio | 1.39 ± 0.44 | 1.36 ± 0.43 |
| Bupropion Erythroamino Alcohol | | |
| $AUC_{0-\tau}$ (ng · hr/mL) | 2145.70 ± 615.22 | 2353.73 ± 645.40 |
| $C_{max}$ (ng/mL) | 109.07 ± 29.98 | 119.37 ± 26.82 |
| $C_{min}$ (ng/mL) | 76.51 ± 25.69 | 85.59 ± 26.63 |
| $T_{max}$ (hours) | 8.37 ± 2.04 | 2.40 ± 0.66 |
| Degree of Fluctuation (%) | 38.11 ± 15.25 | 38.90 ± 33.91 |
| $C_{ave}$ (ng/mL) | 89.40 ± 25.63 | 98.07 ± 26.89 |
| Degree of Swing (%) | 46.04 ± 20.70 | 46.18 ± 43.72 |
| M/P ratio | 1.39 ± 0.44 | 1.36 ± 0.43 |

The relative (modified-release tablets of the invention v. Wellbutrin®) bioavailability analysis results for $AUC_{0-\tau}$ and $C_{max}$ for bupropion and its metabolites transformed using the natural logarithm is summarized in Table 22:

TABLE 22

| Parameter | 90% C.I. | Ratio of Means | Intra-Subject CV | 90% C.I. | Ratio of Means | Intra-Subject CV |
|---|---|---|---|---|---|---|
| | Bupropion | | | Hydroxybupropion | | |
| $AUC_{0-\tau}$ | 86.14%-92.64% | 89.33% | 8.27% | 87.00%-95.42% | 91.11% | 10.49% |
| $C_{max}$ | 91.08%-103.00% | 96.86% | 13.97% | 85.98%-99.90% | 92.68% | 17.04% |
| | Bupropion Threoamino Alcohol | | | Bupropion Erythroamino Alcohol | | |
| $AUC_{0-\tau}$ | 87.17%-94.21% | 90.63% | 8.82% | 87.32%-94.66% | 90.91% | 9.16% |
| $C_{max}$ | 87.42%-97.28% | 92.22% | 12.13% | 84.84%-95.89% | 90.20% | 13.91% |

The data in Tables 21 and 22 show that a 300 mg dosage strength modified-release tablet of the invention administered once daily is bioequivalent to the 100 mg dosage strength immediate release Wellbutrin® administered thrice daily.

EXAMPLE 7

A two-way, steady state, crossover, open-label, multiple-dose, fasting, comparative bioavailability study of the 300 mg modified-release bupropion hydrochloride tablets of the invention versus the commercially available prior art 150 mg Zyban® product in normal healthy non-smoking male and female subjects was carried out. The study was designed to compare the bioavailability of the 300 mg q.d. dosage form of the modified-release bupropion hydrochloride tablets of the invention against the commercially available prior art 150 mg b.i.d. Zyban® tablets.

The study design followed a 2-period, 2-treatment, multiple-dose crossover design under fasting conditions. The study periods were separated by a 2-week washout interval. A total of 54 subjects (40 Male, 14 Female) were enrolled in the study of which 49 of the subjects (37 Male, 12 Female) completed the study. Subjects were administered 150 mg q.d. Zyban® tablets from days 1-3 of the study. Days 4-17 were followed by:

A) 300 mg q.d. modified-release bupropion hydrochloride tablets of the invention.

B) 1.50 mg b.i.d. Zyban® tablets.

The graphical mean plasma-concentration (ng/ml) profiles of bupropion and its metabolites hydroxybupropion, bupropion threoamino alcohol, and erytlroamino alcohol over the study period after administration of the 1×300 mg once daily modified-release tablets of the invention and the 2×150 mg (b.i.d.) Zyban® tablets under fasting conditions are shown in FIGS. 7A-E respectively.

Table 23 provides the mean (±SD) pharmacokinetic data for bupropion following administration of the once daily 300 mg dosage strength modified-release tablet of the invention or the commercially available prior art 150 mg b.i.d. Zyban® tablet:

TABLE 23

| Pharmacokinetic Parameter | Geometric Mean Arithmetic Mean (% CV) | |
|---|---|---|
| | 300 mg Dosage Strength Modified Release Bupropion HCl Tablets of the Invention (n = 49) | Zyban ® 150 mg Tablets (n = 49) |
| $AUC_{0-\tau}$ (ng · hr/mL) | 1412.4767 1464.21 (28.12) | 1561.9651 1617.72 (26.94) |

TABLE 23-continued

| Pharmacokinetic Parameter | Geometric Mean Arithmetic Mean (% CV) | |
|---|---|---|
| | 300 mg Dosage Strength Modified Release Bupropion HCl Tablets of the Invention (n = 49) | Zyban ® 150 mg Tablets (n = 49) |
| $C_{max}$ (ng/mL) | 143.9693 148.81 (26.10) | 135.9517 141.65 (28.36) |

TABLE 23-continued

| Pharmacokinetic Parameter | Geometric Mean / Arithmetic Mean (% CV) | |
|---|---|---|
| | 300 mg Dosage Strength Modified Release Bupropion HCl Tablets of the Invention (n = 49) | Zyban ® 150 mg Tablets (n = 49) |
| $C_{min}$ (ng/mL) | 23.1224 | 25.3277 |
| | 24.50 | 26.85 |
| | (35.46) | (35.28) |
| $T_{max}$ (hours)* | 4.92 | 3.23 |
| | (17.03) | (31.63) |
| Degree of Fluctuation (%)* | 207.65 | 171.85 |
| | (20.47) | (19.27) |
| Degree of Swing (%)* | 551.15 | 449.59 |
| | (37.98) | (26.79) |
| $C_{ave}$ (ng/mL)* | 61.01 | 67.41 |
| | (28.12) | (26.94) |
| MRT (hours)* | 9.63 | 10.23 |
| | (6.57) | (2.90) |
| Hydroxybupropion | | |
| $AUC_{0-\tau}$ (ng · hr/mL) | 19688.697 | 21984.655 |
| | 21255.88 | 23792.58 |
| | (38.44) | (39.17) |
| $C_{max}$ (ng/mL) | 1035.5625 | 1114.0976 |
| | 1111.28 | 1200.37 |
| | (36.14) | (38.41) |
| $C_{min}$ (ng/mL) | 669.3453 | 775.6489 |
| | 731.59 | 847.91 |
| | (41.72) | (42.12) |
| $T_{max}$ (hours)* | 6.61 | 4.26 |
| | (34.52) | (35.36) |
| Degree of Fluctuation (%)* | 44.42 | 36.96 |
| | (35.50) | (50.36) |
| Degree of Swing (%)* | 56.77 | 46.22 |
| | (47.41) | (75.49) |
| $C_{ave}$ (ng/mL)* | 885.66 | 991.36 |
| | (38.44) | (39.17) |
| MRT (hours)* | 11.43 | 11.53 |
| | (2.87) | (1.93) |
| M/P Ratio* | 14.538 | 14.684 |
| | (43.310) | (43.323) |
| Bupropion Threoamino alcohol | | |
| $AUC_{0-\tau}$ (ng · hr/mL) | 9040.7734 | 110398.325 |
| | 9638.64 | 11100.02 |
| | (37.34) | (38.42) |
| $C_{max}$ (ng/mL) | 494.6250 | 542.8864 |
| | 524.91 | 582.74 |
| | (37.35) | (44.35) |
| $C_{min}$ (ng/mL) | 285.9451 | 339.2713 |
| | 311.93 | 370.23 |
| | (43.69) | (45.18) |
| $T_{max}$ (hours)* | 7.74 | 4.45 |
| | (35.60) | (35.77) |
| Degree of Fluctuation (%)* | 55.31 | 47.10 |
| | (32.09) | (32.50) |
| Degree of Swing (%)* | 75.80 | 61.76 |
| | (43.62) | (40.19) |
| $C_{ave}$ (ng/mL)* | 401.61 | 462.50 |
| | (37.34) | (38.42) |
| MRT (hours)* | 11.63 | 11.74 |
| | (2.85) | (1.76) |
| M/P Ratio* | 6.609 | 6.830 |
| | (29.472) | (26.491) |
| Bupropion Erythroamino alcohol | | |
| $AUC_{0-\tau}$ (ng · hr/mL) | 1784.5115 | 2033.8788 |
| | 1875.33 | 2125.14 |
| | (31.95) | (30.18) |
| $C_{max}$ (ng/mL) | 92.4622 | 101.5651 |
| | 97.12 | 105.63 |
| | (32.17) | (28.49) |
| $C_{min}$ (ng/mL) | 61.3442 | 71.6863 |
| | 65.30 | 75.83 |
| | (36.05) | (34.19) |
| $T_{max}$ (hours)* | 8.31 | 4.74 |
| | (38.42) | (42.77) |
| Degree of Fluctuation | 41.87 | 35.10 |
| | (43.18) | (37.78) |
| Degree of Swing (%)* | 53.00 | 43.04 |
| | (54.46) | (50.13) |
| $C_{ave}$ (ng/mL)* | 78.14 | 88.15 |
| | (31.95) | (30.18) |
| MRT (hours)* | 11.73 | 11.73 |
| | (2.63) | (1.87) |
| M/P Ratio* | 1.298 | 1.334 |
| | (27.168) | (25.504) |

*Expressed as arithmetic means (% CV)

The relative (modified-release tablets of the invention v. Zyban®) bioavailability analysis results for $AUC_{0-t}$, $C_{max}$ and $C_{min}$ transformed using the natural logarithm for bupropion and its metabolites is summarized in Table 24:

TABLE 24

| | Bupropion | | | Hydroxybupropion | | |
|---|---|---|---|---|---|---|
| Parameter | 90% C.I. | Ratio of Geometric Means | Intra-Subject CV | 90% C.I. | Ratio of Geometric Means | Intra-Subject CV |
| $AUC_{0-\tau}$ | 87.19%-93.93% | 90.50% | 10.98% | 85.87%-93.26% | 89.49% | 12.17% |
| $C_{max}$ | 99.25%-113.46% | 106.12% | 19.73% | 89.02%-97.00% | 92.93% | 12.66% |
| $C_{min}$ | 85.77%-97.00% | 91.21% | 18.14% | 82.22%-90.34% | 86.19% | 13.88% |

| | Bupropion Threoamino Alcohol | | | Bupropion Erythroamino Alcohol | | |
|---|---|---|---|---|---|---|
| Parameter | 90% C.I. | Ratio of Means | Intra-Subject CV | 90% C.I. | Ratio of Means | Intra-Subject CV |
| $AUC_{0-\tau}$ | 83.91%-90.09% | 86.94% | 10.47% | 84.48%-91.09% | 87.72% | 11.11% |
| $C_{max}$ | 86.76%-95.78% | 91.16% | 14.59% | 86.95%-95.44% | 91.10% | 13.73% |
| $C_{min}$ | 80.45%-88.16% | 84.22% | 13.49% | 81.61%-89.60% | 85.51% | 13.77% |

The data in Tables 23 and 24 show that a 300 mg (q.d.) dosage strength modified-release bupropion hydrochloride tablet of the invention is bioequivalent to the 150 mg b.i.d sustained-release commercially available prior art Zyban® tablet.

EXAMPLE 8 (COMPARATIVE EXAMPLE)

A 150 mg and 300 mg bupropion hydrochloride formulation was prepared as taught in U.S. Pat. No. 6,143,327 and the pharmacokinetic parameters and relative bioavailability data assessed for bioequivalency. The proportions of the components in the core, first and second coat formulations used are as shown in Table 25:

TABLE 25

| Components | 150 mg Mg | 150 mg % of core | 300 mg mg | 300 mg % of core |
|---|---|---|---|---|
| CORE | | | | |
| Bupropion HCl | 150.00 | 93.75 | 300.00 | 93.75 |
| Binder[1] | 5.30 | 3.31 | 10.6 | 3.31 |
| Lubricant[2] | 4.70 | 2.94 | 9.40 | 2.94 |
| Purified Water[3] | 110.00 | * | 220.00 | * |
| Total core weight | 160.00 | 100 | 320.00 | 100.00 |
| FIRST COAT | | | | |
| Water-insoluble water permeable film forming polymer[4] | 10.96 | 60.8 | 14.40 | 60.00% |
| Water-soluble polymer[5] | 4.70 | 26.10 | 6.47 | 26.96 |
| Plasticizer[6] | 2.34 | 13.01 | 3.13 | 13.04 |
| Ethyl Alcohol[3] | 190.00 | * | 230.50 | * |
| Isopropyl Alcohol 99%[3] | 10.00 | * | 12.35 | * |
| Total dry first coat weight | 18.00 | 100.00 | 24.00 | 100.00 |
| SECOND COAT | | | | |
| Methacrylic Acid Copolymer[7] | 7.75 | 63.00 | 11.66 | 63.02 |
| Glidant[8] | 2.30 | 18.70 | 3.45 | 18.65 |
| Plasticizer[9] | 2.25 | 18.30 | 3.39 | 18.32 |
| Purified water[3] | 48.00 | * | 72.20 | * |
| Total dry second coat weight | 12.30 | 100.00 | 18.50 | 100.00 |

[1]Polyvinyl Alcohol
[2]Glyceryl behenate (Compritol 888 ATO)
[3]Evaporated during drying
[4]Ethyl cellulose 100 Premium (Ethocel ®)
[5]Polyvinylpyrrolidone (Kollidon ® 90F)
[6]Polyethylene Glycol 1450 (Carbowax ®)
[7]poly(methacrylic acid, methyl methacrylate) 1:1 (Eudragit ® L 30 D-55)
[8]Plasticizer is a combination of polyethylene glycol 1450 and triethyl citrate in a ratio of 2:1
[9]Silicon Dioxide (Syloid ® 244)

The tablets were manufactured as taught by the '327 patent.

A pilot three-way multiple-dose open-label fasting comparative bioavailability study of bupropion hydrochloride tablets (2×150 mg q.d.) made according to the '327 patent (the '327 patent formulation') versus the commercially available Zyban® sustained-release tablets (1×150 mg b.i.d.) and Wellbutrin® tablets (t.i.d.) in normal healthy smoking and non-smoking male volunteers was conducted. The purpose of the study was to evaluate the relative bioavailability of bupropion hydrochloride 150 mg of the 327 formulation (2×150 mg q.d.) relative to Zyban® 150 mg sustained-release tablets (1×150 mg b.i.d) and Wellbutrin® 100 mg tablets (1×100 mg t.i.d.) under single dose or steady-state fasting conditions.

Table 26 shows the mean (±SD) plasma concentration-time profiles for bupropion (ng/ml) under single dose conditions:

TABLE 26

| Sample Time (hours) | 2 × 150 mg (q.d.) tablet of the '327 patent (A) | Zyban 150 mg SR tablets (1 × 150 mg b.i.d.) (B) | Wellbutrin ® tablet 100 mg (3 × 100 mg t.i.d) (C) |
|---|---|---|---|
| 0.0 | 11.71 ± 3.55 | 8.25 ± 2.74 | 30.01 ± 17.82 |
| 1.0 | 11.08 ± 2.90 | 53.87 ± 14.58 | 113.91 ± 40.96 |
| 2.0 | 12.95 ± 4.38 | 75.96 ± 13.83 | 104.04 ± 20.62 |
| 4.0 | 60.60 ± 24.59 | 83.71 ± 12.49 | 58.45 ± 12.90 |
| 5.0 | ND | ND | 45.92 ± 10.65 |
| 6.0 | 98.23 ± 31.28 | 64.03 ± 13.95 | 85.54 ± 80.91 |
| 7.0 | ND | ND | 104.45 ± 39.11 |
| 8.0 | 82.63 ± 23.84 | 41.69 ± 7.81 | ND |
| 9.0 | ND | ND | 76.79 ± 15.73 |
| 11.0 | ND | ND | 50.28 ± 15.09 |
| 12.0 | 59.47 ± 18.45 | 21.50 ± 4.50 | 110.38 ± 71.29 |
| 13.0 | ND | 51.03 ± 34.38 | 120.69 ± 32.81 |
| 14.0 | ND | 84.04 ± 41.74 | ND |
| 15.0 | ND | ND | 75.30 ± 20.36 |
| 16.0 | ND | 86.15 ± 37.20 | 58.53 ± 15.44 |
| 18.0 | 32.46 ± 9.52 | 55.48 ± 13.29 | ND |
| 20.0 | ND | ND | 33.45 ± 7.40 |
| 24.0 | 20.21 ± 5.28 | 27.81 ± 7.77 | 24.14 ± 6.03 |

Table 27 provides the mean (±SD) pharmacokinetic data for bupropion following administration of the tablets shown in Table 25:

TABLE 27

| Pharmacokinetic Parameter (mean ± SD) | 327 formulation (n = 15) | Zyban ® (n = 15) | Wellbutrin ® (n = 15) |
|---|---|---|---|
| $AUC_{0-24}$ (ng · hr/mL) | 1154.65 ± 244.28 | 1301.05 ± 214.94 | 1622.89 ± 318.02 |
| $C_{max}$ (ng/mL) | 103.77 ± 28.13 | 112.68 ± 37.06 | 163.10 ± 56.84 |
| $T_{max}$ (hrs) | 6.40 ± 1.88 | 11.07 ± 5.85 | 6.87 ± 5.60 |

The relative bioavailability analysis results for $AUC_{0-24}$ (ng·hr/ml), and $C_{max}$ (ng/ml) shown in Table 27, transformed using the natural algorithm is summarized in Table 28:

TABLE 28

| Parameter | AUC$_{0-24}$ | | | C$_{max}$ | | |
|---|---|---|---|---|---|---|
| | 90% C.I. | Ratio of Geometric Means | Intra-Subject C.V. | 90% C.I. | Ratio of Geometric Means | Intra-Subject C.V. |
| 327 formulation vs. Zyban ® | 78%-99% | 88% | 23.65% | 78%-111% | 93% | 31.44% |
| 327 formulation vs. Wellbutrin ® | 63%-80% | 71% | 38.79% | 54%-76% | 64% | 52.35% |

Table 29 shows the mean (±SD) steady-state plasma concentration-time profiles for bupropion (ng/ml) for the tablet composition shown in Table 25:

TABLE 29

| Sample Time (hours) | 2 × 150 mg (q.d.) tablet of the '327 patent | Zyban 150 mg SR tablets (1 × 150 mg b.i.d.) | Wellbutrin ® tablet 100 mg (3 × 100 mg t.i.d) |
|---|---|---|---|
| 0.0 | 0.00 ± 0.00 | 0.00 ± 0.00 | 0.00 ± 0.00 |
| 0.0 | 11.71 ± 3.55 | 8.25 ± 2.74 | 30.01 ± 17.82 |
| 0.0 | 20.21 ± 5.28 | 27.81 ± 7.77 | 24.14 ± 6.03 |
| 0.0 | 22.22 ± 5.80 | 34.12 ± 8.51 | 27.11 ± 8.31 |
| 0.0 | 21.58 ± 6.21 | 32.70 ± 9.94 | 27.33 ± 8.79 |
| 0.0 | 23.44 ± 8.31 | 31.96 ± 8.83 | 28.71 ± 11.05 |
| 1.0 | 21.47 ± 7.06 | 64.22 ± 18.93 | 112.09 ± 29.65 |
| 2.0 | 24.37 ± 8.77 | 90.76 ± 18.63 | 116.66 ± 27.01 |
| 4.0 | 87.61 ± 36.30 | 94.97 ± 19.30 | 61.94 ± 16.35 |
| 5.0 | ND | ND | 49.43 ± 13.56 |
| 6.0 | 101.39 ± 25.48 | 73.35 ± 17.94 | 85.34 ± 52.23 |
| 7.0 | ND | ND | 112.05 ± 46.38 |
| 8.0 | 77.06 ± 16.40 | 52.56 ± 11.74 | ND |
| 9.0 | ND | ND | 87.11 ± 23.77 |
| 11.0 | ND | ND | 55.49 ± 17.50 |
| 12.0 | 58.88 ± 16.23 | 31.23 ± 9.05 | 115.93 ± 53.59 |
| 13.0 | ND | 58.01 ± 21.81 | 117.74 ± 39.87 |
| 14.0 | ND | 105.36 ± 42.68 | ND |
| 15.0 | ND | ND | 74.33 ± 17.77 |
| 16.0 | ND | 93.55 ± 23.49 | 60.45 ± 14.56 |
| 18.0 | 34.69 ± 8.82 | 65.80 ± 14.61 | ND |
| 20.0 | ND | ND | 39.86 ± 12.55 |
| 24.0 | 23.30 ± 6.75 | 33.15 ± 9.39 | 29.49 ± 10.09 |
| 48.0 | 8.80 ± 4.20 | 12.02 ± 4.84 | 11.11 ± 4.68 |
| 72.0 | 4.61 ± 2.60 | 5.75 ± 3.06 | 5.59 ± 2.75 |
| 96.0 | 2.25 ± 1.82 | 3.03 ± 2.01 | 2.35 ± 1.45 |
| 120.0 | 1.01 ± 1.12 | 1.43 ± 1.44 | 1.35 ± 1.53 |

Table 30 shows the mean (±SD) pharmacokinetic data for bupropion under steady state conditions following administration of the tablets shown in Table 25:

TABLE 30

| Pharmacokinetic Parameter (mean ± SD) | 327 formulation (n = 15) | Zyban ® (n = 15) | Wellbutrin ® (n = 15) |
|---|---|---|---|
| AUC$_{0-24}$ (ng · hr/mL) | 1251.45 ± 257.24 | 1554.77 ± 293.70 | 1728.31 ± 374.54 |
| C$_{max}$ (ng/mL) | 112.24 ± 26.42 | 119.77 ± 27.76 | 156.19 ± 32.27 |
| T$_{max}$ (hrs) | 5.33 ± 1.23 | 11.47 ± 5.04 | 9.00 ± 4.14 |

The relative bioavailability analysis results for AUC$_{0-24}$ (ng·hr/ml), and C$_{max}$ (ng/ml) shown in Table 30, transformed using the natural algorithm is summarized in Table 31:

TABLE 31

| Parameter | AUC$_{(0-24)}$ | | | C$_{max}$ | | |
|---|---|---|---|---|---|---|
| | 90% C.I. | Ratio of Geometric Means | Intra-Subject C.V. | 90% C.I. | Ratio of Geometric Means | Intra-Subject C.V. |
| 327 formulation vs Zyban ® | 71%-91% | 80% | 20.06% | 82%-108% | 94% | 22.65% |
| 327 formulation vs Wellbutrin ® | 64%-82% | 73% | 20.06% | 62%-82% | 72% | 22.65% |

The pharmacokinetic and relative bioavailability data show that the 90% CI for the formulation as taught in the '327 patent does not fall within the FDA suggested 80%-125% range for a product to be bioequivalent. Accordingly, the data show that the '327 patent formulation is not bioequivalent to the commercially available Zyban®/Wellbutrin® SR or Wellbutrin® tablets.

The invention claimed is:

1. A modified-release tablet comprising:
   (i) a core comprising an effective amount of bupropion hydrochloride, polyvinyl alcohol, and glyceryl behenate, wherein said bupropion hydrochloride is present in an amount of at least about 94% by weight of the core dry weight, said polyvinyl alcohol is present in an amount of about 3% by weight of the core dry weight, and said glyceryl behenate is present in an amount of about 3% by weight of each core dry weight;
   (ii) a control-releasing coat completely surrounding and contacting said core, said control-releasing coat comprising ethyl cellulose grade PR 100, polyethylene glycol 1450, and polyvinylpyrrolidone, wherein said ethyl cellulose grade PR 100 is present in an amount of from about 45% to about 50% by weight of the control-releasing coating dry weight, said polyethylene glycol 1450 is present in an amount of about 12% by weight of the control-releasing coating dry weight, and said polyvinylpyrrolidone is present in an amount of from about 25% to about 50% of the control-releasing coat dry weight, wherein the amount of said control-releasing coat applied is from about 9% to about 15% by weight of the dry tablet core; and
   (iii) a moisture barrier surrounding said control-releasing coat, said moisture barrier comprising methacrylic acid copolymer, polyethylene glycol 1450, triethyl citrate and silicon dioxide, wherein said methacrylic acid copolymer is present in an amount of about 66% by weight of said moisture barrier dry weight, said polyethylene glycol 1450 and triethyl citrate is present in an amount of about 10% by weight of said moisture barrier dry weight in a proportion of 1 part triethyl citrate to 2 parts polyethylene glycol 1450, and said silicon dioxide is present in an amount of about 25% by weight of said moisture barrier dry weight, wherein the amount of the said moisture barrier applied is no more than about 2.5% of the tablet dry weight,
   wherein the tablet provides an extended-release of the bupropion hydrochloride such that after about 2 hours about 5% of the bupropion hydrochloride content is released, after about 4 hours about 32% of the bupropion hydrochloride content is released, after about 8 hours about 74% of the bupropion hydrochloride content is released and after about 16 hours no less than about 99% of the bupropion hydrochloride content is released,
   and wherein the ratio of the ethyl cellulose grade PR 100: polyethylene glycol 1450:polyvinylpyrrolidone is from about 3:1:4 to about 5:1:3.

2. The modified release tablet of claim 1 wherein said modified-release tablet provides a $C_{max}$ of bupropion in the blood plasma at between about 3 hours and about 8 hours ($T_{max}$) after administration in the fasted state.

3. The modified-release tablet of claim 1 wherein said modified-release tablet provides a $C_{max}$ of bupropion ranging from about 60 ng/ml to about 280 ng/ml in the blood plasma at about 5 hours ($T_{max}$) after administration of a once daily 300 mg dose of said modified-release bupropion hydrochloride tablet or a 2×150 mg dose once daily of said modified-release bupropion hydrochloride tablet in the fasted state.

4. The modified-release tablet of claim 1 wherein said modified-release tablet exhibits an $AUC_{(0-t)}$ for bupropion from about 800 ng.hr/ml to about 2850 ng.hr/ml after administration of a once daily 300 mg dose of said modified-release bupropion hydrochloride tablet or a 2×150 mg dose once daily of said modified-release bupropion hydrochloride tablet in the fasted state.

5. The modified-release tablet of claim 1 wherein said modified-release tablet exhibits an $AUC_{(0-inf)}$ for bupropion from about 840 ng.hr/ml to about 3000 ng.hr/ml after administration of a once daily 300 mg dose of said modified-release bupropion hydrochloride tablet or a 2×150 mg dose once daily of said modified-release bupropion hydrochloride tablet in the fasted state.

6. The modified-release tablet of claim 1 which when administered in a once-daily bupropion treatment regimen to a patient in need of treatment provides a $C_{max}$ for bupropion ranging from about 60 ng/ml to about 280 ng/ml at between 3 hours and 8 hours ($T_{max}$) and an $AUC_{(0-t)}$ for bupropion ranging from about 800 ng.hr/ml to about 2850 ng.hr/ml.

7. The modified-release tablet of claim 1 wherein the moisture content of said modified-release tablet is no more than about 0.4 % in said tablet when stored at 40° C.±2° C./75% RH±5% RH in an open dish after about 10 days.

8. The modified-release tablet of claim 1 wherein the moisture content of said modified-release tablet is no more than about 1% in said tablet when stored at 40° C.±2° C./75% RH±5% RH after storage for about 6 months.

9. The modified-release tablet of claim 1 wherein said modified-release tablet contains at least about 95% undegraded bupropion hydrochloride after storage for 12 months at about 25° C.±2° C./60% RH±5% RH.

10. The modified-release tablet of claim 1 wherein said modified-release tablet contains at least about 95% undegraded bupropion hydrochloride after storage for 18 months at about 25° C.±2° C./60% RH±5% RH.

11. The modified-release tablet of claim 1, wherein said tablet contains 150 mg of bupropion hydrochloride.

12. The modified-release tablet of claim 1, wherein said tablet contains 300 mg of bupropion hydrochloride.

13. The modified release tablet of claim 1 which does not exhibit any food effects.

14. A method of treating depression in a patient in need thereof comprising administering to the patient the modified-release tablet of claim 1.

15. The method of claim 14 wherein said modified-release tablet contains a 300 mg dose.

16. The method of claim 14 wherein said modified-release tablet contains a 150 mg dose.

* * * * *